US005173492A

United States Patent [19]

Suzuki et al.

[11] Patent Number: 5,173,492

[45] Date of Patent: Dec. 22, 1992

[54] S-TRIAZOLO(3,4-I)PURINE DERIVATIVES

[75] Inventors: Fumio Suzuki, Mishima; Junichi Shimada, Shizuoka; Kenji Ohmori, Mishima; Haruhiko Manabe; Kazuihiro Kubo, both of Shizuoka, all of Japan; Akira Karasawa, Huntingdon Valley, Pa.; Tetsuji Ohno, Shizuoka; Shizuo Shiozaki, Fuji; Akio Ishii, Shizuoka; Katsuichi Shuto, Mishima, all of Japan

[73] Assignee: Kyowa Hakko Kogyo Co., Ltd., Tokyo, Japan

[21] Appl. No.: 752,180

[22] Filed: Aug. 23, 1991

Related U.S. Application Data

[63] Continuation of Ser. No. 581,562, Sep. 12, 1990, abandoned.

[30] Foreign Application Priority Data

Sep. 14, 1989 [JP] Japan ................................ 1-239117
Oct. 6, 1989 [JP] Japan ................................ 1-261761

[51] Int. Cl.$^5$ .................. A61K 31/505; C07D 239/70
[52] U.S. Cl. .................................... 514/267; 544/251
[58] Field of Search ......................... 544/251; 514/267

[56] References Cited

FOREIGN PATENT DOCUMENTS 1095906 2/1981 Canada ................................ 544/251
0002370 4/1988 World Int. Prop. O. .......... 544/251

OTHER PUBLICATIONS

Brown et al, Aust. J. Chem. 35, 1263-7, 1982.
Carroll et al; J. Org. Chem. 30, 3601-3603 1965.
Brown et al., 3 Alkylthio-s-triazolo[3,4-i]purines and 9-Alkylbis-s-triazolo [3,4-b:3,', 4'-i]purines, *Aust. J. Chem.*, 1982, 1263-7.

*Primary Examiner*—Robert T. Bond
*Assistant Examiner*—Y. N. Gupta
*Attorney, Agent, or Firm*—Fitzpatrick, Cella, Harper & Scinto

[57] ABSTRACT

There are disclosed s-triazolo[3,4-i]purine derivatives represented by formula:

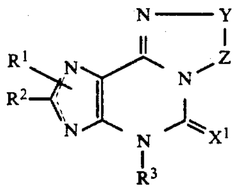

wherein Y-Z represents

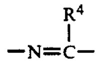 or 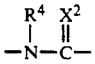

$R_4$ represents hydrogen, alkyl, substituted or unsubstituted aromatic heterocyclic group or substituted or unsubstituted aryl; and $X^2$ represents oxygen, sulfur or NH; each of $R^1$ and $R^2$ independently represents hydrogen, alkyl, cycloalkyl, aralkyl or substituted or unsubstituted aryl; $R^3$ represents alkyl, cycloalkyl, aralkyl or substituted or unsubstituted aryl; $X^1$ represents oxygen or sulfur; and · · · · represents a single bond or a double bond or pharmaceutically acceptable salts thereof.

10 Claims, No Drawings

S-TRIAZOLO(3,4-I)PURINE DERIVATIVES

This application is a continuation of application Ser. No. 581,562 filed Sep. 12, 1990, now abandoned.

BACKGROUND OF THE INVENTION

The present invention relates to novel s-triazolo[3,4-i]purine derivatives which possess a broncho-dilatory activity, diuretic activity, renal protecting activity and/or anti-amnestic activity.

As s-triazolo[3,4-i]purine derivatives represented by the following formula:

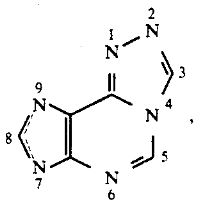

9H-s-triazolo[3,4-i]purine which has no substituents at the 3-, 5-, 7- and 8-positions and s-triazolo[3,4-i]purine derivatives which have benzyl at the 7- or 9-position are disclosed in J. Org. Chem., 30, 3601 (1965); and 3- alkylthio-s-triazolo[3,4-i]purine having SH, $SCH_3$ or $SCH_2CONH_2$ at the 3-position is disclosed in Aust. J. Chem., 35, 1263 (1982). As yet their pharmacological activities are unknown. Furthermore, s-triazolo[3,4-i]purine derivatives having a substituent at the 5-position thereof have not been reported so far.

SUMMARY OF THE INVENTION

An object of the present invention is to provide novel s-triazolo[3,4-i]purine derivatives having an bronchodilatory effect, anti-asthmatic effect, diuretic effect, renal protecting effect and/or anti-amnestic effect.

The present invention is directed to s-triazolo [3,4-i]purine derivatives represented by formula (I):

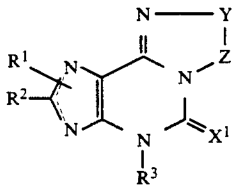

(I)

wherein X-Z represents

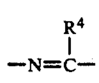 or 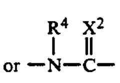

$R^4$ represents hydrogen, alkyl, substituted or unsubstituted aromatic heterocyclic group or substituted or unsubstituted aryl; and $X^2$ represents oxygen, sulfur or NH;

each of $R^1$ and $R^2$ independently represents hydrogen, alkyl, cycloalkyl, aralkyl or substituted or unsubstituted aryl;

$R^3$ represents alkyl, cycloalkyl, aralkyl or substituted or unsubstituted aryl;

$X^1$ represents oxygen or sulfur;

and · · · · represents a single bond or a double bond or pharmaceutically acceptable salts thereof.

DETAIELD DESCRIPTION OF THE INVENTION

In the definitions of the groups in formula (I), the alkyl means a straight or branched alkyl having 1 to 10 carbon atoms, for example, methyl, ethyl, propyl, isopropyl, butyl, isobutyl, sec-butyl, tert-butyl, pentyl neopentyl, hexyl, heptyl, octyl, nonyl, decyl, etc. The cycloalkyl includes an alicyclic alkyl having 3 to 8 carbon atoms such as cyclopropyl,cyclobutyl, cyclopentyl, cyclohexyl, cyclooctyl, etc. The aralkyl includes aralkyls having 7 to 15 carbon atoms such as benzyl, phenethyl, benzhydryl, etc. The aryl includes aryls having 6 to 10 carbon atoms such as phenyl, naphthyl, etc. The substituent in the substituted aryl includes one or two of the same or different lower alkyl, trifluoromethyl, hydroxyl, lower alkoxyl, lower alkylthio, nitro, halogen, amino, lower alkylamino, lower alkanoylamino, aroylamino, carboxyl, lower alkoxycarbonyl, lower alkanoyl and aroyl, etc. The aromatic heterocyclic group includes heterocyclic rings of 5- or 6-members such as thienyl, furyl, pyrazolyl, oxazolyl, imidazolyl, pyridyl, etc. The substituent in the substituted heterocyclic group includes one or two of the same or different lower alkyl, lower alkoxyl, halogen, etc.

The lower alkyl and the alkyl moiety in the lower alkoxyl, lower alkylthio, lower alkylamino and lower alkoxycarbonyl mean a straight or branched alkyl having 1 to 6 carbon atoms such as methyl, ethyl, propyl, isopropyl, butyl, isobutyl, sec-butyl, tert-butyl, pentyl, neopentyl, hexyl, etc.

The lower alkanoyl and the alkanoyl moiety in the lower alkanoylamino include alkanoyl having 1 to 6 carbaon atoms such as formyl, acetyl, propionyl, butyryl, isobutyl, pivaloyl, valeryl, isovaleryl, etc.

The aroyl and the aroyl moiety in the aroylamino include, for example, benzoyl, toluyl, propylbenzoyl, naphthoyl, etc.

The halogen means fluorine, chlorine, bromine and iodine.

The salts of Compound (I) include pharmaceutically acceptable acid addition salts, metal salts, ammonium salts, organic amine addition salts, amino acid addition salts, etc.

The pharmaceutically acceptable acid addition salts of Compound (I), include inorganic acid salt such as hydrochloride, sulfate, phosphate, etc. and organic acid salts such as acetate, maleate, fumarate, tartarate, citrate, etc. The pharmaceutically acceptable metal salts include alkali metal salts such as sodium salt, potassium salt etc.; alkaline earth metal salts such as magnesium salt, calcium salt, etc. and further an aluminum salt and a zinc salt. The pharmaceutically acceptable organic amine addition salts include addition salt of morpholine, piperidine, etc. The pharmaceutically acceptable amino acid addition salts, include lysine, glycine, phenylalanine, etc.

The methods for preparing Compound (I) are described below.

When the defined groups are changed under the conditions of the following processes or are inadequate to proceeding of the following processes, processes can be readily carried out by a usual method in the organic synthetic chemistry, for example, by protection of functional groups, elimination of protecting groups.

Process 1

Compound (Ia), which is Compound (I) where Y-Z is

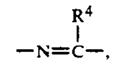

is synthesized according to Steps 1 and 2:

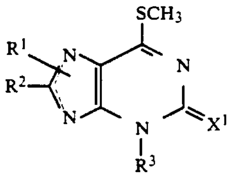

(II)

$R^4CONHNH_2$ (III)
Step 1

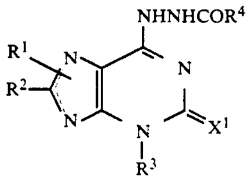

(IV)

Step 2

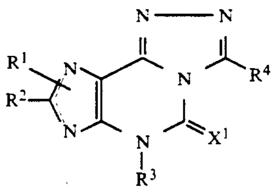

(Ia)

wherein $X^1$, $R^1$, $R^2$, $R^3$ and $R^4$ have the same significance as described above.

(Step 1)

Compound (IV) is obtained by reacting Compound (II) with Compound (III).

Any solvent is used so long as it is inert to the reaction. The solvent includes, for example, dimethylalkanamides such as dimethylformamide, dimethylacetamide, etc.; ketones such as acetone, methyl ethyl ketone, etc.; aromatic hydrocarbons such as toluene, xylene, etc.; halogenated hydrocarbons such as dichloroethane, 1,1,2,2-tetrachloroethane, etc.; dimethylsulfoxide, etc. The solvent is used alone or in combination. The reaction is performed at 50° to 200° C. and completed in 10 minutes to 72 hours.

(Step 2)

Compound (Ia) is obtained by cyclization of Compound (IV). The reaction is performed in a solvent in the presence of an acid catalyst.

The acid catalyst includes, for example, hydrochloric acid, sulfuric acid, sulfonic acid such as p-toluenesulfonic acid, camphor sulfonic acid, etc., or silica gel powders. The acid catalyst is used alone or in combination.

Any solvent is used so long as it is inert to the reaction. The solvent includes aromatic hydrocarbons such as toluene, xylene, etc.; halogenated hydrocarbons such as dichloroethane, 1,1,2,2-tetrachloroethane, etc.; dimethylsulfoxide, etc. The solvent is used alone or in combination. The reaction is performed at 50° to 150° C. and completed in 10 minutes to 4 hours.

Compounds (IIa) and (IIb), among the starting Compound (II) wherein $X^1$ is oxygen is prepared by the method of Kleiner et al. [J. Chem. Soc., Perkin I, 739 (1973)]or by a modified method of Kleiner et al. The reaction steps are illustrated as follows:

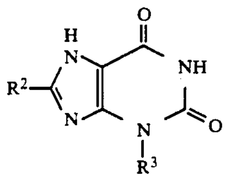

(V)

$P_2S_5$

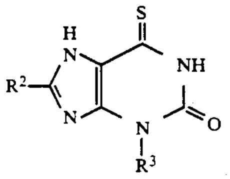

(VI)

$CH_3I$

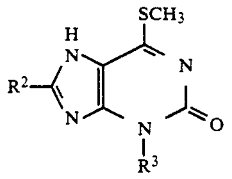

(IIa)

$R^{1a}$—L

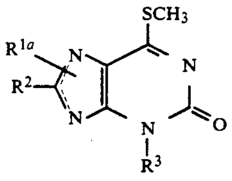

(IIb)

wherein $R^{1a}$ represents a group other than hydrogen in the definition for $R^1$ described above; $R^2$ and $R^3$ have the same significance as described above; and L represents a leaving group.

The leaving group denoted by L includes, for example, halogen atom such as chlorine, bromine, iodine, etc.; alkylsulfonyloxy such as methanesulfonyloxy, etc.; arylsulfonyloxy such as phenylsulfonyloxy, p-toluenesulfonyloxy, etc.

Compound (V) in step 2 is synthesized by a notorious method [Biochemistry, 16, 3316 (1977)]or its modified method.

The starting Compound (IIc), which is Compound (II) where $X^1$ is sulfur is synthesized by the method of Jacobson et al. [J. Med. Chem., 32, 1873 (1989)]or by a modified method of Jacobson et al.

Process 2

Compound (Ia) is also synthesized by reacting Compound (VII) with Compound (VIII). The reaction is performed in the presence or absence of solvent

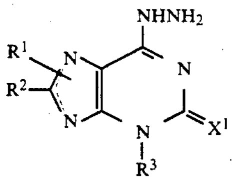

(VII)

(wherein $X^1$, $R^1$, $R^2$ and $R^3$ have the same significance as described above).

$R^4C(OR^5)_3$ (VIII)

(wherein $R^4$ has the same significance as described above and $R^5$ represents alkyl having 1 to 10 carbon atoms.

Any solvent is used so long as it is inert to the reaction. The solvent includes, for example, ethers such as tetrahydrofuran, dioxane, etc.; dimethylalkanamides such as dimethylformamide, dimethylacetamide, etc.; alcohols such as methanol, ethanol, isopropyl alcohol, etc.; halogenated hydrocarbons such as dichloroethane, 1,1,2,2-tetrachloroethane, etc.; dimethylsulfoxide, etc. The solvent is used alone or in combination.

The reaction is performed at 50° to 150° C. and completed in 10 minutes to 4 hours.

The starting Compound (VII) is prepared from Compound (II) according to a modification of the notorious method as described in Il Farmaco Ed. Sci., 40, 221 (1985).

The reaction is performed as follows:

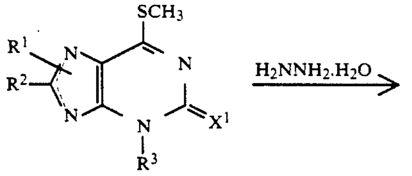

(II)

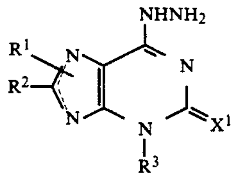

(VII)

(wherein $X^1$, $R^1$, $R^2$ and $R^3$ have the same significance as described above).

Process 3

Compound (Ib1) which is Compound (I) wherein

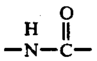

is synthesized according to the following step:

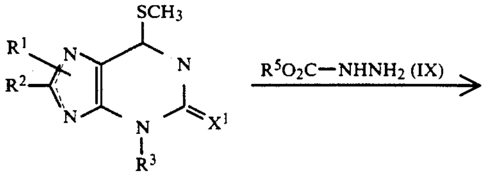

(II)

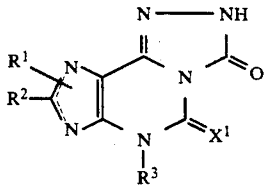

(Ib1)

(wherein $R^1$, $R^2$, $R^3$, $R^5$ and $X^1$ have the same significance as described above.

Compound (Ib1) is obtained by reacting Compound (II) with Compound (IX).

Any solvent is used so long as it is inert to the reaction. The solvent includes, for example, dimethylalkanamides such as dimethylformamide, dimethylacetamide, etc.; ketones such as acetone, methyl ethyl ketone, etc.; aromatic hydrocarbons such as toluene, xylene, etc.; halogenated hydrocarbons such as dichloroethane, 1,1,2,2-tetrachloroethane, etc.; dimethylsulfoxide, etc. The solvent is used alone or in combination. The reaction is performed at 50° to 200° C. and completed in 10 minutes to 12 hours.

The starting Compound (II) is obtained by the process shown in Process 1.

The starting Compound (IX) is commercially available.

Process 4

Compound (Ib1) is also synthesized by the following steps:

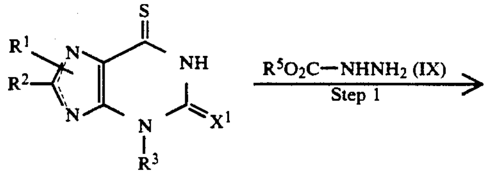

(X)

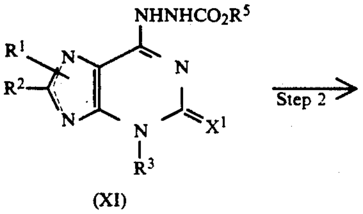

(XI)

-continued

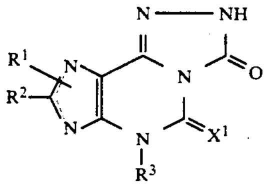

(Ib1)

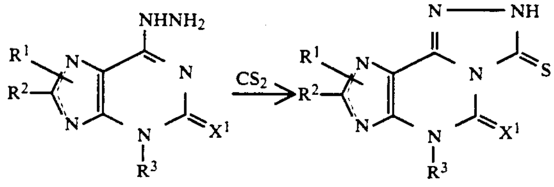

(VII) (Ib2)

(wherein $R^1$, $R^2$, $R^3$, $R^5$ and $X^1$ have the same significance as described above).

(Step 1)

Compound (XI) is obtained by reacting Compound (X) with Compound (IX).

Any solvent is used so long as it is inert to the reaction. The solvent includes, for example, dimethylalkanamides such as dimethylformamide, dimethylacetamide, etc.; alcohols such as methanol, ethanol, n-butanol, etc.; ketones such as acetone, methyl ethyl ketone, etc.; aromatic hydrocarbons such as toluene, xylene, etc.; halogenated hydrocarbons such as dichloroethane, 1,1,2,2-tetrachloroethane, etc.; dimethylsulfoxide, etc. The solvent is used alone or in combination.

The reaction is carried out at 50° to 200° C. and completed in 1 to 48 hours.

The starting Compound (Xa), which is Compound (X) wherein $X^1$ is oxygen can be prepared by the method of Reichman et al. [J. Chem. Soc., Perkin I, 2647 (1973)] or, by the method of Woodridge et al. [J. Chem. Soc., 1863 (1962)] or by a modification of these methods.

The starting Compound (Xb), which is Compound (X) wherein $X^1$ is sulfur can be prepared by the method of Jacobson et al. [J. Med. Chem., 32, 1873 (1989)] or by a modified method of Jacobson et al.

(Step 2)

Compound (Ibl) is obtained by cyclization of Compound (XI). The reaction is performed under heating in the presence or absence of a solvent. Any solvent is used so long as it is inert to the reaction. The solvent includes, for example, dimethylalkanamides such as dimethylformamide, dimethylacetamide, etc.; alcohols such as methanol, ethanol, n-butanol, etc.; dimethylsulfoxide, etc. The solvent is used alone or is combination.

The reaction is carried out at 100° to 200° C. and completed in 1 to 24 hours.

Process 5

Compound (Ib2) which is Compound (I) wherein Y-Z

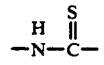

is synthesized by the following step;

(wherein $R^1$, $R^2$, $R^3$ and $X^1$ have the same significance as described above).

Compound (Ib2) can be synthesized by reacting Compound (VII) with carbon disulfide in the presence of or absence of a solvent. Any solvent is used so long as it is inert to the reaction. The solvent includes, for example, pyridines such as pyridine, quinoline, etc.; dimethylalkanamides such as dimethylformamide, dimethylacetamide, etc.; dimethylsulfoxide, etc. The solvent is used alone or in combination.

The reaction is performed at 50° to 200° C. and completed in 10 minutes to 5 hours.

The starting Compound (VII) is obtained by the process shown in Process 2.

Process 6

Compound (Ib3), which is Compound (I) wherein Y-Z is

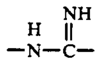

is synthesized by the following step:

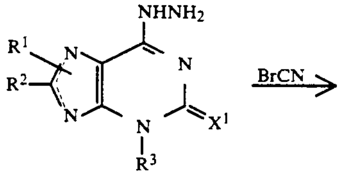

(VII)

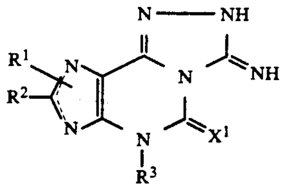

(Ib3)

(wherein $R^1$, $R^2$, $R^3$ and $X^1$ have the same significance as described above.)

Compound (Ib3) can be synthesized by reacting Compound (VII) with cyanogen bromide.

Any solvent is used so long as it is inert to the reaction. The solvent includes, for example alcohols such as methanol, ethanol, etc.; ethers such as dioxane, tetrahydrofuran, etc., aliphatic nitriles such as acetonitrile, propionitrile, etc.; dimethylalkanamides such as dimethylformamide, dimethylacetamide, etc. The solvent is used alone or in combination.

The reaction is performed at 50° to 200° C. and completed in 10 minutes to 5 hours.

Process 7

Compound (Ib4) which is Compound (I) wherein Y-Z is

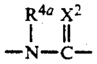

is obtained by the following step:

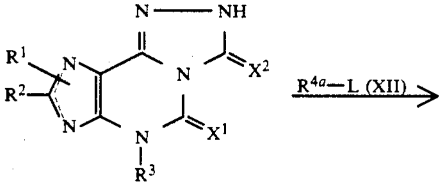

(Ib1), (Ib2), (Ib3)

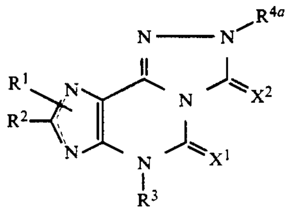

(Ib4)

(wherein $R^1$, $R^2$, $R^3$, $X^1$ and $X^2$ have the same significance as described above, and $R^{4a}$ represents a group other than hydrogen in the definition of $R^4$ described above).

Compound (Ib4) can be synthesized by reacting Compound (Ibl), (Ib2) or (Ib3) with Compound (XII) in a solvent. The reaction is performed preferably in the presence of a base. Any solvent is used so long as it is inert to the reaction. The solvent includes, for example, ethers such as tetrahydrofuran, dioxane,etc., dimethylalkanamides such as dimethylformamide, dimethylacetamide, etc; alcohols such as methanol, ethanol, isopropyl alcohol, etc.; or dimethylsulfoxide, etc. The solvent is used alone or in combination. The base includes alkali metal carbonates such as potassium carbonate, sodium carbonate, etc.; hydrated alkali metals such as sodium hydride, potassium hydride, etc.; alkali metal alkoxides such as sodium methoxide, sodium ethoxide, etc. The reaction is performed at 0° to 150° C. and completed in 10 minutes to 12 hours.

Process 8

Compound (Id), which is Compound (I) wherein $R^{1a}$ represents a group other than hydrogen in the definition of $R^1$ is obtained by the following step.

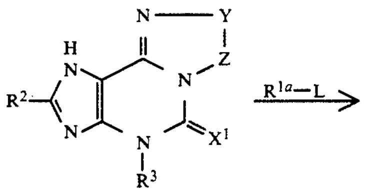

(Ic)

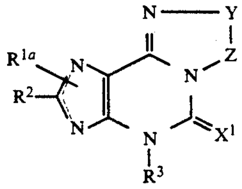

(Id)

(wherein $R^{1a}$ represents a group other than hydrogen in the definition of $R^1$ described above and, $X^1$, $R^2$, $R^3$ and L have the same significance as described above).

Compound (Id) can be synthesized by reacting Compound (Ic), which is Compound (I) wherein $R^1$ is hydrogen, with $R^{1a}$-L, preferably in the presence of a base.

Any solvent is used so long as it is inert to the reaction. The solvent includes, for example, ethers such as tetrahydrofuran, dioxane,etc., dimethylalkanamides such as dimethylformamide, dimethylacetamide, etc.; alcohols such as methanol, ethanol, isopropyl alcohol, etc.; or dimethylsulfoxide, etc. The solvent is used alone or in combination. The base includes alkali metal carbonates such as potassium carbonate, sodium carbonate, etc.; hydrated alkali metals such as sodium hydride, potassium hydride, etc.; alkali metal alkoxides such as sodium methoxide, sodium ethoxide, etc.

The reaction is performed at 0° to 150° C. and completed in 10 minutes to 12 hours.

The intermediates and objective compounds in the respective methods described above is isolated and purified by purification methods conventionally used in organic synthetic chemistry, for example, filtration, extraction, drying, concentration, recrystallization, various column chromatographies, etc. The intermediates can be directly used in the subsequent reaction, without any particular purification.

In the case that it is desired to obtain salts of Compound (I), when Compound (I) is obtained in the form of its salt, Compound (I) is purified as it is. When Compound (I) is obtained in the free form, its salts are formed in a conventional manner, for example, Compound (I) is suspended or dissolved in an appropriate solvent, and an acid or base is added to the solution or suspension.

Furthermore, Compound (I) and pharmaceutically acceptable salts thereof may exist in the form of addition products to water or various solvents; in this case, the pharmaceutically acceptable salts are also included in the present invention.

Furthermore, Compounds (Ibl), (Ib2) and (Ib3) wherein $R^4$ is hydrogen may be present in the form of Compound (Ibt) as tautomers.

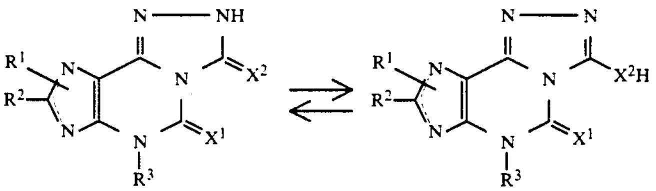

(Ib1), (Ib2), (Ib3) (Ibt)

All the possible stereoisomers including the tautomers and mixtures are also included in the scope of the present invention.

Specific examples of Compound (I) obtained by the various methods are shown in Table 1.

TABLE 1-1

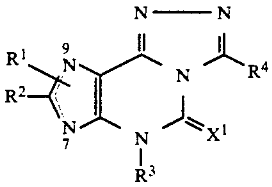

| Compound No. | $R^1$ | $R^2$ | $R^3$ | $R^4$ | $X^1$ |
|---|---|---|---|---|---|
| 1 | 9-$CH_3$ | H | $(CH_2)_2CH_3$ | 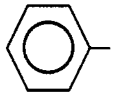 | O |
| 2 | 9-$CH_3$ | H | $(CH_2)_2CH_3$ | 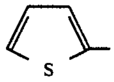 | O |
| 3 | 9-$CH_3$ | H | $(CH_2)_2CH_3$ | 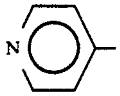 | O |
| 4 | 9-$CH_3$ | H | $(CH_2)_2CH_3$ | 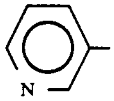 | O |
| 5 | 9-$CH_3$ | H | $(CH_2)_2CH_3$ | 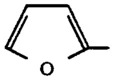 | O |
| 6 | 9-$CH_3$ | H | $(CH_2)_2CH_3$ | 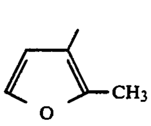 | O |
| 7 | 9-$CH_3$ | H | $(CH_2)_2CH_3$ | 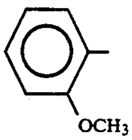 | O |
| 8 | 9-$CH_3$ | H | $(CH_2)_2CH_3$ | 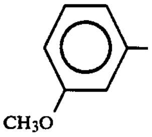 | O |

TABLE 1-1-continued
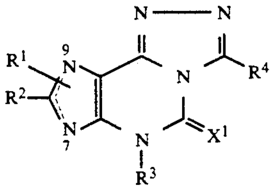
| Compound No. | $R^1$ | $R^2$ | $R^3$ | $R^4$ | $X^1$ |
|---|---|---|---|---|---|
| 9 | 9-$CH_3$ | H | $(CH_2)_2CH_3$ | 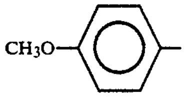 | O |
| 10 | 9-$CH_3$ | H | $(CH_2)_2CH_3$ | 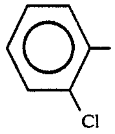 | O |
| 11 | 9-$CH_3$ | H | $(CH_2)_2CH_3$ | 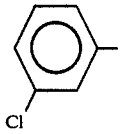 | O |
| 12 | 9-$CH_3$ | H | $(CH_2)_2CH_3$ | 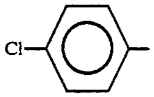 | O |
| 13 | 9-$CH_3$ | H | $(CH_2)_2CH_3$ | 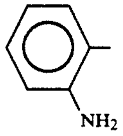 | O |
| 14 | 9-$CH_3$ | H | $(CH_2)_2CH_3$ | 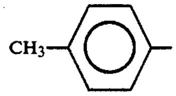 | O |
| 15 | 9-$CH_3$ | H | $(CH_2)_2CH_3$ | 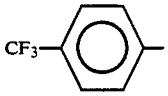 | O |
| 16 | 9-$CH_3$ | H | $(CH_2)_2CH_3$ | 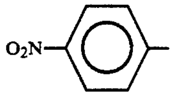 | O |
| 17 | 9-$CH_3$ | H | $(CH_2)_2CH_3$ | 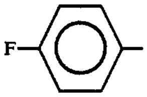 | O |
| 18 | 9-$CH_3$ | H | $(CH_2)_2CH_3$ | 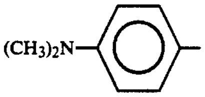 | O |

TABLE 1-1-continued
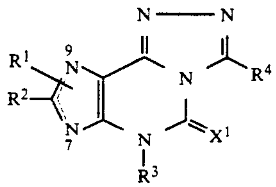
| Compound No. | $R^1$ | $R^2$ | $R^3$ | $R^4$ | $X^1$ |
|---|---|---|---|---|---|
| 19 | 9-$CH_3$ | H | $(CH_2)_2CH_3$ | 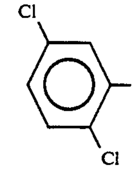 | O |
| 20 | 9-$CH_3$ | H | $(CH_2)_2CH_3$ | 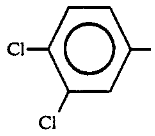 | O |
| 21 | 9-$CH_3$ | H | $(CH_2)_2CH_3$ | 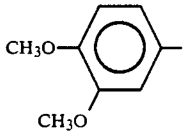 | O |
| 22 | 9-$CH_3$ | H | $(CH_2)_2CH_3$ | 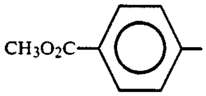 | O |
| 23 | 9-$CH_3$ | H | $(CH_2)_2CH_3$ | 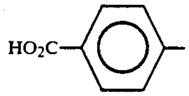 | O |
| 24 | 9-$CH_3$ | H | $(CH_2)_2CH_3$ | $CH_3$ | O |
| 25 | H | H | $(CH_2)_2CH_3$ | $CH_3$ | O |
| 26 | H | 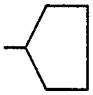 | $(CH_2)_2CH_3$ | 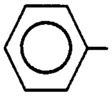 | O |
| 27 | H | 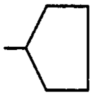 | $(CH_2)_2CH_3$ | $CH_3$ | O |
| 28 | 9-$CH_3$ | H | 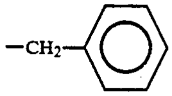 | 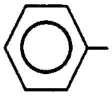 | O |
| 29 | 9-$CH_3$ | H | 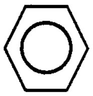 | 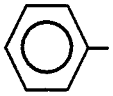 | O |
| 30 | H | H | $(CH_2)_2CH_3$ | 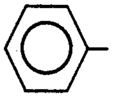 | O |

TABLE 1-1-continued
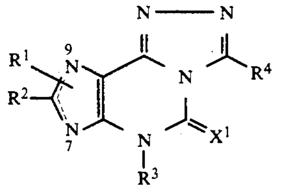
| Compound No. | $R^1$ | $R^2$ | $R^3$ | $R^4$ | $X^1$ |
|---|---|---|---|---|---|
| 31 | H | H | $(CH_2)_2CH_3$ | 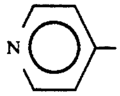 | O |
| 32 | H | H | $(CH_2)_2CH_3$ | 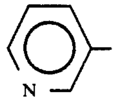 | O |
| 33 | H | H | $(CH_2)_2CH_3$ | 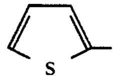 | O |
| 34 | H | H | 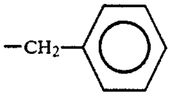 | 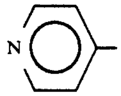 | O |
| 35 | 9-$(CH_2)_2CH_3$ | H | $(CH_2)_2CH_3$ | 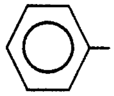 | O |
| 36 | 9-$CH_3$ | H | $(CH_2)_2CH_3$ | H | O |
| 37 | 9-$CH_3$ | H | 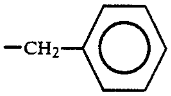 | $CH_3$ | O |
| 38 | H | H | $(CH_2)_3CH_3$ | 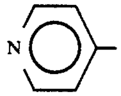 | O |
| 39 | 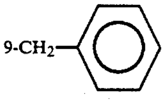 | H | $(CH_2)_2CH_3$ | 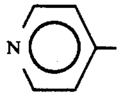 | O |
| 40 | 9-$(CH_2)_2CH_3$ | H | $(CH_2)_2CH_3$ | 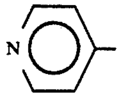 | O |

TABLE 1-2

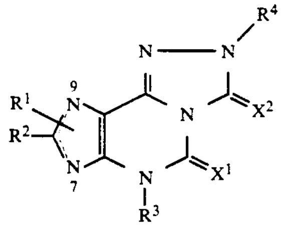

| Compound No. | $R^1$ | $R^2$ | $R^3$ | $X^1$ | $X^2$ | $R^4$ |
|---|---|---|---|---|---|---|
| 41 | 9-$CH_3$ | H | $CH_3(CH_2)_2$ | O | O | H |
| 42 | 9-$CH_3$ | H | 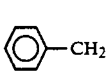 | O | O | H |
| 43 | H | 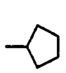 | $CH_3(CH_2)_2$ | O | O | H |
| 44 | 9-$(CH_2)_2CH_3$ | H | $CH_3(CH_2)_2$ | O | O | H |
| 45 | H | H | $CH_3(CH_2)_2$ | O | O | H |
| 46 | 9-$CH_3$ | H | $CH_3(CH_2)_2$ | O | S | H |
| 47 | 9-$CH_3$ | H | 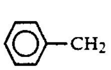 | O | S | H |
| 48 | 9-$CH_3$ | H | $CH_3(CH_2)_2$ | O | O | $C_2H_5$ |
| 49 | 9-$CH_3$ | H | 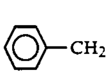 | O | O | $C_2H_5$ |
| 50 | 9-$CH_3$ | H | $CH_3(CH_2)_2$ | O | NH | H |
| 51 | 9-$CH_3$ | H | $CH_3(CH_2)_2$ | O | O | H |

The pharmacological activities of Compound (I) represented by the general formula (I) are illustrated as follows.

(a) Effects on passive Schultz-Dale reaction (broncho dilatory effects)

Guinea pigs were passively sensitized as follows. Hartley male guinea pigs weighing 350 to 500 g were injected intraperitoneally with rabbit anti-egg albumin (EWA) serum prepared by the method of Koda et al. [Folia pharmacol., Japon 66, 237, (1970)]. After 24 hours, the guinea pigs were stunned and exsanguinated, and then trachea was excised. The zig-zag strips of the trachea were prepared by the method of Emmerson and Mackay [J. Pharm. Pharmacol., 31, 798, (1979)]. The strips were suspended in Krebs-Henseleit solution at 37° C under aeration of a mixed gas of 95% oxygen and 5% carbon dioxide, ahd incubated for one hour. Antigen (EWA) was then introduced in the solution (final concentration; 1 μg/ml), and the contraction was measured by isotonictrasducer (TD-112s, made by Nihon Kohden K.K., Japan) and recorded on a recorder (Type 3066, made by Yokogawa-Hokushin Denki, K.K. Japan). After the contraction curves reached plateau the compounds were successively added in order to get cumulative concentration-relaxation curves. Concentration of 50% relaxation rate ($IC_{50}$) was calculated from the regression line, which was obtained from cumulative concentration-relaxation.curves.

The results are shown in Table 2.

(b) Effects on experimental asthma

Guinea pigs were passively sensitized as follows. Hartley male guinea pigs weighing 350 to 500 g were intraperitoneally injected with 1 ml of rabbit anti-egg alubmin (EWA) serum prepared by the method of Koda et al. [Folia pharmacol., Japon, 66, 237 (1970)]. The animals were treated with intraperitoneal injection of diphenhydramine (20 mg/kg) and propranolol (5 mg/kg), 30 minutes before administration of test compounds. 17 hours after the sensitization, the test compounds (50 mg/kg or 5 mg/kg) or saline (control) were orally administrated to sensitized animals. After one hour from the administration of the test compounds, the guinea pigs were placed in plastic observation box and were exposed to an aerosal antigen of 1.5% EWA.

The time until the onset of respiratory distress-like symptom [collapse time (second)] was measured as a result of experimental asthma.

The results are shown in Table 2.

(c) Inhibition effect on platelet activating factor (PAF)

-induced mortality

The experiment was performed by a minor modification of method of Carlson et al. [Agents and Actions, 21, 379 (1987)]. Groups each consisting of 10 male dd mice (weighing 28 to 32 g) were used, and 100 mg/kg of test compound or a saline (control) was orally administrated. One hour after the administration of test compound, 40 μg/kg of PAF (manufactured by Avanti Polar Lipids Co., Ltd.) was intravenously administered. Two hours after PAF injection, the mortality rate of the animals was observed. The compound whose mortality rate was significantly ($p < 0.05$: Fischer's accurate probability tests) lower than control is regarded as having inhibitory effect on PAF-induced mortality, and the results in Table 2 were represented by minimum effective dose (MED).

TABLE 2

| Compound | Passive Schultz-Dale reaction $IC_{50}$ (μM) | Experimental asthma Collapse time (sec) $n = 3 - 10$ mean ± S.E.M. | PAF-induced mortality MED (mg/kg) |
|---|---|---|---|
| 1 | 4.1 | | |
| 2 | 0.40 | | |
| 3 | 0.032 | 422 ± 130 | |
| 4 | 7.7 | 358 ± 65 | |
| 5 | 0.70 | | 100 |
| 6 | | | 100 |
| 8 | 5.6 | | |
| 9 | 7.8 | | |
| 10 | 18 | | |
| 11 | >40 | | 100 |
| 12 | 26 | 399 ± 55** | 100 |
| 14 | 45 | | |
| 24 | | | 100 |
| 25 | 0.42 | 590 ± 9.8 | 100 |
| 30 | 0.76 | | 10 |
| 31 | 11 | 512 ± 52 | 25 |
| 38 | >40 | 401 ± 78 | 25 |
| 44 | 39.6 | | |
| Theophylline* | 23 | 414 ± 47 | 100 |
| Control | | 254 ± 18 | |

*The Merck Index 11th 9212 (1989)

**Administration dose of Compound 12 was 5 mg/kg (Administration dose of the other compounds were 50 mg/kg)

(d) Diuretic activity

Wistar male rats weighing 150 to 300 g were used after fasting for 18 horus. A test compound or saline (control) was orally administered to rats (dose: 25 mg/kg) and urine was taken for 6 hours. The test was performed using 3 groups per test compound, and each group consists of 3 animals. The urine was metered by a measuring cylinder and electrolytes ($Na+$ and $K+$) in the urine were analyzed by flame photometer (model 775A: Hitachi Ltd.).

The results are shown in Table 3.

Parameters in Table 3 are represented by relative value for control.

TABLE 3

| Compound | Urine volume (%) | Excretion of $Na^+$ (%) | Excretion of $K^+$ (%) | $Na^+/K^+$ |
|---|---|---|---|---|
| Control | 100 | 100 | 100 | 1.00 |
| 1 | 255 | 226 | 87 | 3.18 |
| 3 | 274 | 224 | 196 | 1.09 |
| 4 | 177 | 167 | 134 | 1.25 |
| 6 | 223 | 240 | 146 | 1.64 |
| 7 | 173 | 162 | 122 | 1.33 |
| 8 | 170 | 175 | 122 | 1.44 |
| 9 | 253 | 219 | 139 | 1.57 |
| 10 | 162 | 134 | 109 | 1.24 |
| 11 | 255 | 302 | 134 | 2.26 |
| 12 | 198 | 183 | 129 | 1.42 |
| 16 | 170 | 194 | 175 | 1.11 |
| 17 | 178 | 179 | 134 | 1.42 |
| 18 | 155 | 141 | 129 | 1.09 |
| 24 | 160 | 148 | 168 | 1.23 |
| 25 | 161 | 193 | 119 | 1.63 |
| 29 | 170 | 155 | 110 | 1.41 |
| 30 | 204 | 220 | 124 | 1.77 |
| 31 | 191 | 196 | 118 | 1.66 |
| 38 | 353 | 293 | 180 | 1.63 |
| 32 | 195 | 196 | 129 | 1.52 |
| 39 | 185 | 184 | 145 | 1.27 |
| 40Sa* | 155 | 132 | 136 | 0.97 |
| 44 | 191 | 142 | 128 | 1.11 |
| 49 | 300 | 279 | 173 | 1.61 |
| 51 | 200 | 152 | 152 | 1.00 |
| Furosemide** | 175 | 164 | 157 | 1.05 |

*40Sa is hydrochloride salt of Compound 40.
**The Merck Index 11th 4221 (1989).

(e) Effect on renal protecting activity (glycerol-induced renal deficient model)

Renal insufficiency is the condition that homeostasis of body fluid failed to maintain by disorder of renal function. It is well known that subcutaneous or intramuscular administration of glycerol to rat induce actue renal insufficiency characterized by renal tubular distrubance [Can J. Physiol. Pharmacol., 65, 42 (1987)].

Wistar male rats (fasted both food and water for 18 horus) were used. A test compound or saline (control) was intraperitoneally administered (dose: 0.1 ml/100 g) to rats. After 30 minutes rats were anesthesized with ether and the back skin was picked up and 0.8 ml/100 g of 50% glycerol was subcutaneously administered. 24 hours after the glycerol injection, the rats were anesthesized with ether and 5 ml of the blood was collected from the descending aorta. To obtain the serum, after allowing it to stand for 30 minutes or longer, the blood sample was centrifuged at 3000 rpm for 10 minutes. Creatinine in the serum sample was determined using autoanalyzer (AU510, Olympus) or clinical analysis kit of creatinine (Creatinine Test Wako; by Wako Pure Chemical Ind., Japan). Urea nitrogen in the serum was determined using autoanalyzer (AU510; made by Olympus Optical Co., Ltd, Japan) or clinical analysis kit of urea nitrogen (Urea nitrogen test wako; by Wako Pure Chemical Ind., Japan).

The results are shown in Table 4.

Further, the left kidneys of test compound treated groups and control groups were taken out from the animals and the kidneys were prepared for pathological sample.

As the result of patholozic autopsy for kidneys, it was indicated that the renal insufficiency was improved by the test compounds as shown in Table 4.

TABLE 4

| Compound No. | Creatinine in serum (mg/dl) Glycerol treated | | Urea nitrogen in serum (mg/dl) Glycerol treated | |
|---|---|---|---|---|
| | Control | Test compound administrated (Significance for control*) | Control | Test compound administrated (Significance for control*) |
| 3 | 2.64 ± 0.27 | 1.90 ± 0.15 ($p < 0.05$) | | |
| 4 | 2.64 ± 0.27 | 1.80 ± 0.11 ($p < 0.05$) | | |
| 6 | 4.76 ± 0.18 | 2.76 ± 0.27 ($p < 0.001$) | 171.1 ± 7.7 | 100.8 ± 9.3 ($p < 0.001$) |
| 7 | 4.06 ± 0.30 | 2.96 ± 0.30 ($p < 0.05$) | 143.4 ± 8.1 | 119.9 ± 11.3 ($p < 0.05$) |
| 8 | 4.09 ± 0.29 | 1.97 ± 0.23 ($p < 0.001$) | 137.9 ± 7.2 | 76.4 ± 9.6 ($p < 0.001$) |
| 10 | 5.01 ± 0.19 | 2.81 ± 0.33 ($p < 0.001$) | | |
| 11 | 4.09 ± 0.29 | 2.22 ± 0.16 ($p < 0.001$) | 137.9 ± 7.2 | 91.1 ± 7.8 ($p < 0.001$) |
| 14 | 4.09 ± 0.29 | 2.91 ± 0.41 ($p < 0.05$) | 137.9 ± 7.2 | 115.9 ± 16.5 N.S. |
| 19 | 4.06 ± 0.30 | 2.73 ± 0.38 ($p < 0.05$) | 143.4 ± 8.1 | 99.1 ± 12.7 ($p < 0.01$) |
| 20 | 3.17 ± 0.28 | 1.89 ± 0.33 ($p < 0.001$) | 131.9 ± 9.0 | 70.9 ± 17.1 ($p < 0.01$) |
| 28 | 5.01 ± 0.19 | 2.68 ± 0.35 ($P < 0.001$) | | |
| 31 | 5.01 ± 0.19 | 3.05 ± 0.31 ($P < 0.001$) | | |
| 42 | 3.17 ± 0.28 | 2.19 ± 0.14 ($p < 0.01$) | 131.9 ± 9.0 | 81.4 ± 9.6 ($p < 0.01$) |
| 44 | 3.17 ± 0.28 | 2.10 ± 0.20 ($p < 0.01$) | 131.9 ± 9.0 | 75.9 ± 17.2 ($p < 0.01$) |
| Amino-phylline** | 2.03 ± 0.18 | 1.72 ± 0.07 N.S. | 46.2 ± 6.5 | 30.6 ± 2.0 ($P < 0.05$) |
| Furo-cemide*** | 3.22 ± 0.35 | 4.17 ± 0.41 N.S. | 110.7 ± 9.4 | 150.3 ± 13.7 ($p < 0.05$) |
| Normal control | Glycerol untreated 0.50 ± 0.02 | | Glycerol untreated 15.2 ± 0.9 | |

*Student-t test was used for level of significance
**The Merck Index 11th 477 (1989)
***The Merck Index 11th 4221 (1989)
N.S. No significant difference (f) Effect on electroconvulsive shock (ECS)-induced amnesia:

Male ddy mice (weighing 23 to 29 g) were used and each group consists of 14 to 15 animals. These tests were performed with a step through type passive avoidance apparatus. As experimental apparatus, two rooms (bright and dark) with automatic management system were used. An experimental apparatus is composed of a bright room equipped with 4W of fluorescent light (15×9×11 cm) and a dark room (15×14×18 cm), the two rooms are separated by a guillotine door of 3×3 cm. The floor of both rooms is stainless steal grid floor and the weak electric current can be send the grid floor of dark room. In the automatic management system, latency of acquisition trial and test trial are measured automatically by controlling with a controller (TK-402, by UNICOM, Japan).

The test compound was dissolved in saline and saline was used as a control. The test compound and the saline (control) were orally administered 60 minutes before the acquisition trial, respectively.

Acquisition trial for learning was performed as follows. An animal placed in the bright room could enter, through the door into the dark room that had a grid on the floor. As soon as the mouse entered the dark room, a scrambled foot-shock (0.18 mA) was delivered to the floor grid for 2 seconds. In the test trial, given 24 hours after the acquisition trial, the animal was again placed in the bright room and the response latency to enter the dark room was measured. The mice which required over 60 seconds to move from the bright room into the dark room were excluded from the test trial. Immediately after the acquisition trial, electric convulsive shock (ECS) (25 mA, 0.2 second, 2000 V) was loaded on mice. The test trial was performed 24 hours after the ECS treatment as follows. The mice received the acquisition trial were placed in the bright room and, latency from the door opening to the entrance of the whole body of animal into the dark room was measured. The maximum measurement time was 600 seconds and latency exceeding 600 seconds was recorded as 600 seconds.

The results are shown in Table 5.

Statistical significance between the control group and test compound treated group was judged by Man Whitney U-test.

TABLE 5

| Test Compound | Dose of test compound (mg/kg) | ECS treatment | Number of animals | Latency of test trial: (Sec) mean ± S.E.M. | Latency of test trial: Comparison of test compound with control |
|---|---|---|---|---|---|
| Normal | 0 | – | 15 | 529.3 ± 26.1 | |
| Control | 0 | + | 30 | 70.9 ± 13.5 | $p < 0.001$* |
| Compound 41 | 0.625 | + | 15 | 105.9 ± 44.0 | No significance |
| | 2.5 | + | 15 | 111.3 ± 20.1 | $p < 0.05$ |
| | 10 | + | 15 | 97.4 ± 38.7 | No significance |
| | 40 | + | 15 | 171.8 ± 43.1 | $p < 0.01$ |

*Comparison of control with normal (g) Effect on scopolamine-induced amnesia

Acquisition trial was performed in a manner similar to Experiment (f). Amnestic treatment was performed by intraperitoneal administration of scopolamine (0.5 mg/kg), 30 minutes pior to the acquisition trial. The test trial was performed 24 hours after the acquisition trial and its latency was determiend as in Experiment (f).

Preparation of administrated test compound was performed in a manner similar to Experiment (f). Test compound and the saline were orally administered 60 minutes before the acquisition trial, respectively.

The results are shown in Table 6.

TABLE 6

| Test Compound | Dose of test compound (mg/kg) | Scopolamine treatment | Number of animals | Latency of test trial: (Sec) mean ± S.E.M. | Latency of test trial: Comparison of test compound with control |
|---|---|---|---|---|---|
| Normal | 0 | – | 30 | 582.6 ± 11.1 | |
| Control | 0 | + | 30 | 40.9 ± 8.1 | $p < 0.001$* |
| Compound 41 | 0.625 | + | 30 | 96.8 ± 21.5 | $p < 0.01$ |
| | 2.5 | + | 30 | 115.8 ± 26.6 | $p < 0.01$ |
| | 10 | + | 30 | 53.4 ± 8.9 | $p < 0.05$ |
| | 40 | + | 30 | 74.3 ± 18.8 | No significance |
| Control | 0 | + | 45 | 37.0 ± 6.2 | $p < 0.001$* |
| Compound 51 | 0.625 | + | 15 | 37.0 ± 11.2 | No significance |
| | 2.5 | + | 15 | 69.5 ± 16.6 | $p < 0.01$ |
| | 10 | + | 15 | 139.9 ± 45.1 | $p < 0.001$ |
| | 40 | + | 15 | 166.3 ± 49.9 | $p < 0.0001$ |

*Comparison of control with normal (h) Acute toxicity

The compounds were orally administrated to male dd-mice weighing 20±1 g. Minimum lethal dose (MLD) was determined by observing the mortality for seven days after the administration.

The results are shown in Table 7.

TABLE 7

| Compound No. | MLD (mg/kg) |
|---|---|
| 1 | 100 |
| 2 | 300 |
| 3 | 100 |
| 4 | 200 |
| 5 | >300 |
| 6 | 200 |
| 7 | 300 |
| 8 | >300 |
| 9 | >300 |
| 10 | 300 |
| 11 | >300 |
| 12 | >300 |
| 13 | >300 |
| 14 | >300 |
| 15 | >300 |
| 16 | >300 |
| 17 | >300 |
| 18 | >300 |
| 19 | >300 |
| 20 | >300 |
| 21 | >300 |
| 22 | >300 |
| 23 | >300 |
| 24 | 300 |
| 25 | 100 |
| 26 | >300 |
| 27 | >300 |
| 28 | >300 |
| 29 | >300 |
| 30 | 300 |
| 31 | >300 |
| 33 | >300 |
| 36 | 300 |
| 37 | >300 |
| 38 | >300 |
| 39 | >300 |
| 40Sa* | 100 |
| 41 | >300 |
| 42 | >300 |
| 43 | >300 |
| 44 | >300 |
| 46 | >300 |
| 48 | >300 |
| 51 | >300 |

*40Sa is hydrochloride of Compound 40.

Compounds (I) or their pharmaceutically acceptable salts are used directly or in various dosage forms. In the present invention, pharmaceutical compositions are prepared by homogeneously mixing an effective amount of Compound (I) or its pharmaceutically acceptable salt with pharmaceutically acceptable carrier. It is desirable that the pharmaceutical compositions are an appropriative dosable unit for oral administration or injection administration.

In the preparation of orally administrated forms, any of useful pharmaceutically acceptable carriers are used. In the case of orally administrated liquid preparates such as suspensions and syrups, for example, water, saccharides such as sucrose, sorbitol, fructose, etc., glycols such as polyethyleneglycol, propyleneglycol, etc., oils such as sesame oil, olive oil, soybean oil, etc., antiseptics such as p-hydroxybenzoic acid esters, etc., and flavors such as strawberry flavor, peppermint etc. are used. In the case of powder, pills, capsules and tablets; vehicles such as lactose, glucose, sucrose, mannitol, etc.; disintegrators such as starch, sodium alginate, etc.; lubricants such as magnesium stearate, talc, etc.; binders such as polyvinyl alcohol, hydroxypropyl cellulose, gelatin, etc., surfactants such as fatty acid esters etc., and plasticizers such as glycerine, etc., are used. Tablets and capsules are most useful dosage form for oral administration because of easy administration. In the preparation of tablets and capsules, solid medicament carriers are used.

Injection solutions are prepared with such a carrier as distilled water, a salt solution, a glucose solution, or a mixture of a salt solution and a glucose solution.

Effective dose and the number of administration of Compound (I) or its pharmaceutically acceptable salt depend on modes of administration and ages, body weight, and symptoms, etc. of patients. It is preferable to usually administer 1 to 50 mg/kg of Compound (I) or its pharmaceutically acceptable salt daily in 2 to 3 portions.

Furthermore, Compound (I) is administrated by inhalation in the form of aerosol, finely pulverized powders, or spray solution. In the case of aerosol administration, the present compound are dissolved in a pharmaceutically acceptable solvent, for example, ethyl alcohol or a combination of miscible solvents and then mixed with a pharmaceutically acceptable propellant. The aerosol composition is used by filling it in a pressure-withstanding container composition. It is preferable that the aerosol valve is a metering valve for discharging an effective dosage of aerosol composition as determined in advance.

The present invention will be described in detail below, referring to Examples and Reference Examples.

Hereafter the present invention is described by referring to the examples and the reference examples.

EXAMPLE 1

6,9-Dihydro-9-methyl-3-phenyl-6-n-propyl -5H-1,2,4-triazolo [3,4-i]-5-one (Compound 1)

After 3.00 g (12.6 mmol) of Compound a prepared in Reference Example 1 was suspended in 75 ml of toluene, 1.72 g (12.6 mmol) of benzoylhydrazine was added to the suspension. The mixture was refluxed for 65 hours under heating. After cooling, 200 ml of chloroform and 100 ml of a 50% saturated aqueous sodium bicarbonate aqueous solution were added, and extracted twice with 50 ml of chloroform. The extracts were combined, then the mixture was washed with a saturated aqueous sodium chloride, dried over anhydrous sodium sulfate, and concentrated. The residue was recrystallized from ethanol to afford 2.48 g (yield, 60%) of 6-(N'-benzoylhydrazino)-3,7-dihydro -7-methyl-3-n-propyl-2H-purin-2-one (Compound ma) as white needles.

Melting point: 228.9°-231.1° C.

Elemental analysis: as $C_{16}H_{18}N_6O_2$.

| | | | |
|---|---|---|---|
| Found (%): | C 59.05 | H 5.68 | N 25.84 |
| Calcd. (%): | C 59.88 | H 5.56 | N 25.75 |

IR (KBr) νmax ($cm^{-1}$): 1691, 1655, 1627, 1575.

$^1$H-NMR (DMSO-$d_6$) δ(ppm): 10.63(s, 1H), 10.41(s, 1H), 7.92-7.84(m, 2H), 7.81(s, 1H), 7.55-7.46(m, 3H), 3.93(s, 3H), 3.81(t, 2H), 1.75-1.55(m, 2H), 0.88 (t, 3H).

After 160 ml of toluene and 308 mg (1.62 mmol) of p-toluenesulfonic acid were added to 2.64 g (8.10 mmol) of the Compound ma, the mixture was refluxed for 2 hours under heating. Then 150 ml of a saturated aqueous sodium bicarbonate solution was added to the mixture. After insoluble matters were filtered off, the filtrate was extracted twice with 50 ml of chloroform and the combined extracts were dried over anhydrous sodium sulfate. The solvent was evaporated under reduced pressure. Recrystallization from ethanol-water gave 1.68 g (yield, 67%) of Compound 1 as white needles.

Melting point: 144.6°-146.1° C. (ethanol-water).

Elemental analysis: as $C_{16}H_{16}N_6O0.2H_2O$.

| | | | |
|---|---|---|---|
| Found (%): | C 61.37 | H 5.11 | N 27.01 |
| Calcd. (%): | C 61.37 | H 5.11 | N 26.94 |

IR (KBr) νmax ($cm^{-1}$): 3430(br), 1725, 1650, 1450.

$^1$H-NMR ($CDCl_3$) δ(ppm): 7.75-7.65(m, 2H), 7.61(s, 1H), 7.55-7.40(m, 3H), 4.20(s, 3H), 4.25-4.15(m, 2H), 1.95-1.75(m, 2H), 0.99(t, 3H).

$^{13}$C-NMR ($CDCl_3$) δ(ppm): 151.3, 144.7, 143.3, 143.1, 139.6, 130.6, 130.1, 127.7, 127.2, 104.1, 45.5, 34.2, 21.3, 11.1.

EXAMPLE 2

6,9-Dihydro-9-methyl-6-n-propyl-3-(2-thienyl)-5H-1,2,4-triazolo[3,4-i]purin-5-one (Compound 2)

After 4.00 g (16.8 mmol ) of Compound a prepared in Reference Example 1 was suspended in 15 ml of dimethylsulfoxide, 2.87 g (20.2 mmol ) of thiophene-2-carboxylic hydrazide was added to the suspension. The mixture was stirred at 160° C. for 30 minutes. After cooling, 400 ml of water and 150 ml of chloroform were added to the reaction mixture. The precipitates were collected by filtration to give 4.53 g of a light yellow powder. The NMR studies identified the powder as a mixture (approximately 9 :1) of 3,7-dihydro-7-methyl-3-n-propyl-6-[N'-(2-thienoyl)hydrazino]-2H-purin-2-one (Compound mb) and Compound 2. To 2.30 g of the mixture were added 20 ml of toluene, 20 ml of 1,1,2,2-tetrachloroethane and 659 mg (3.46 mmol ) of p-toluenesulfonic acid monohydrate, then the solution was refluxed for 4 hours under heating. After cooling, the solution was concentrated, then 50 ml of chloroform and 50 ml of a saturated aqueous sodium bicarbonate were added. The aqueous layer was extracted twice with 50 ml of chloroform, and the extracts were combined and washed with saturated aqueous sodium chloride solution. After drying over anhydrous sodium sulfate, the solvent was evaporated under reduced pressure. Recrystallization from acetonitrile gave 1.57 g (yield, 58%) of Compound 2 as a light yellow powder.

Melting point: 206.2°-207.1° C. (acetonitrile)

Elemental analysis: as $C_{14}H_{14}N_6OS$.

| | | | |
|---|---|---|---|
| Found (%): | C 52.94 | H 4.56 | N 26.40 |
| Calcd. (%): | C 52.88 | H 4.56 | N 26.43 |

IR (KBr) νmax ($cm^{-1}$): 1718, 1658.

$^1$H-NMR (DMSO-$d_6$) δ(ppm): 8.07(s, 1H), 7.92(dd, 1H, J=3.7, 2.0Hz), 7.76(dd, 1H, J=5.1, 2.0Hz), 7.20 (dd, 1H, J=5.1, 3.7Hz), 4.08(t, 2H), 4.06(s, 3H), 1.90-1.70(m, 2H), 0.92(t, 3H.

The substantially same operations as in Example 2 were performed in Examples 3 to 22 except that acylhydrazide shown in Table 8 was used in an equimolar amount instead of thiophene-2-carboxylic hydrazide.

The physicochemical data of Compounds 3 to 22 were given in Table 9.

EXAMPLE 3

6,9-Dihydro-9-methyl-6-n-propyl-3-(4-pyridyl)-5H-1,2,4-triazolo[3,4-i]purin-5-one (Compound 3).

EXAMPLE 4

6,9-Dihydro-9-methyl-6-n-propyl-3-(3-pyridyl)-5H-1,2,4-triazolo[3,4-i]purin-5-one (Compound 4).

EXAMPLE 5

6,9-Dihydro-3-(2-furyl)-9-methyl-6-n-propyl-5H-1,2,4-triazolo[3,4-i]purin-5-one (Compound 5).

EXAMPLE 6

6,9-Dihydro-9-methyl-3-(2-methyl-3-furyl)-6-n-propyl-5H-1,2,4-triazolo[3,4-i]purin-5-one (Compound 6).

EXAMPLE 7

6,9-Dihydro-3-(2-methoxyphenyl)-9-methyl -6-n-propyl-5H-1,2,4-triazolo[3,4-i]purin-5-one (Compound 7).

EXAMPLE 8

6,9-Dihydro-3-(3-methoxyphenyl)-9-methyl -6-n-propyl-5H-1,2,4-triazolo[3,4-i]purin -5-one (Compound 8).

EXAMPLE 9

6,9-Dihydro-3-(4-methoxyphenyl)-9-methyl -6-n-propyl-5H-1,2,4-triazolo[3,4-i]purin -5-one (Compound 9).

EXAMPLE 10

3-(2-Chlorophenyl)-6,9-Dihydro-9-methyl -6-n-propyl-5H-2,4-triazolo[3,4-i]purin-5-one (Compound 10).

EXAMPLE 11

3-(3-Chlorophenyl)-6,9-dihydro-9-methyl -6-n-propyl-5H-1,2,4-triazolo[3,4-i]purin -5-one (Compound 11).

EXAMPLE 12

3-(4-Chlorophenyl)-6,9-dihydro-9-methyl -6-n-propyl-5H-1,2,4-triazolo[3,4-i]purin -5-one (Compound 12).

EXAMPLE 13

3-(2-Aminophenyl)-6,9-dihydro-9-methyl -6-n-propyl-5H-1,2,4-triazolo[3,4-i]purin-5-one (Compound 13).

EXAMPLE 14

6,9-Dihydro-9-methyl-3-(4-methylphenyl) -6-n-propyl-5H-1,2,4-triazolo[3,4-i]purin-5-one (Compound 14).

EXAMPLE 15

6,9-Dihydro-9-methyl-6-n-propyl-3-(4-trifluoromethyl-phenyl)-5H-1,2,4-triazolo[3,4-i]purin-5-one (Compound 15).

EXAMPLE 16

6,9-Dihydro-9-methyl-3-(4-nitrophenyl) -6-n-propyl-5H-1,2,4-triazolo[3,4-i]purin -5-one (Compound 16).

EXAMPLE 17

6,9-Dihydro-3-(4-fluorophenyl)-9-methyl -6-n-propyl-5H-1,2,4-triazolo[3,4-i]purin-5-one (Compound 17).

EXAMPLE 18

6,9-Dihydro-3-(4-dimethylaminophenyl)-9-methyl-6-n-propyl-5H-1,2,4-triazolo[3,4-i]purin-5-one (Compound 18).

EXAMPLE 19

3-(2,5-Dichlorophenyl)-6,9-dihydro-9-methyl-6-n-propyl-H-1,2,4-triazolo[3,4-i]purin-5-one (Compound 19).

EXAMPLE 20

3-(3,4-Dichlorophenyl)-6,9-dihydro-9-methyl -6-n-propyl-5H-1,2,4-triazolo[3,4-i]purin -5-one (Compound 20).

EXAMPLE 21

6,9-Dihydro-3-(3,4-dimethoxyphenyl)-9-methyl-6-n-propyl-5H-1,2,4-triazolo[3,4-i]purin-5-one (Compound 21).

EXAMPLE 22

6,9-Dihydro-3-(4-methoxycarbonylphenyl)-9-methyl-6-n-propyl-5H-1,2,4-triazolo[3,4-i]purin-5-one (Compound 22).

TABLE 8

| Example No. | Acyl hydrazide | Yield (%) |
|---|---|---|
| 3 | Isonicotinic hydrazide | 43 |

TABLE 8-continued

| Example No. | Acyl hydrazide | Yield (%) |
|---|---|---|
| 4 | Nicotinic hydrazide | 15 |
| 5 | 2-Furoic hydrazide | 59 |
| 6 | 3-Methyl-2-furoic hydrazide | 69 |
| 7 | 2-Methoxybenzoic hydrazide | 60 |
| 8 | 3-Methoxybenzoic hydrazide | 43 |
| 9 | 4-Methoxybenzoic hydrazide | 63 |
| 10 | 2-Chlorobenzoic hydrazide | 58 |
| 11 | 3-Chlorobenzoic hydrazide | 33 |
| 12 | 4-Chlorobenzoic hydrazide | 49 |
| 13 | 2-Aminobenzoic hydrazide | 60 |
| 14 | 4-Methylbenzoic hydrazide | 39 |
| 15 | 4-Trifluoromethylbenzoic hydrazide | 80 |
| 16 | 4-Nitrobenzoic hydrazide | 39 |
| 17 | 4-Fluorobenzoic hydrazide | 62 |
| 18 | 4-(N,N-Dimethylamino)benzoic hydrazide | 64 |
| 19 | 2,5-Dichlorobenzoic hydrazide | 96 |
| 20 | 3,4-Dichlorobenzoic hydrazide | 75 |
| 21 | 3,4-Dimethoxybenzoic hydrazide | 69 |
| 22 | 4-Carbomethoxybenzoic hydrazide | 76 |

TABLE 9

| Compound No. | Properties | Melting point (°C.) (Recrystallization solvent) | Elemental analysis (%) (upper: found lower: calcd.) | IR (KBr) $cm^{-1}$ | MS (m/e) Relative intensity | $^1$H-NMR (Measuring solvent) δ (ppm) |
|---|---|---|---|---|---|---|
| 3 | light yellow powder | 236.8–238.4 (Ethanol · Acetonitril) | $C_{15}H_{15}N_7O.0.8C_2H_3N$<br>C H N<br>58.20 4.91 32.15<br>58.27 5.13 31.93 | 1718, 1650 | — | (DMSO-$d_6$) 8.72 (d, 2H, J=4.8Hz), 8.12(s, 1H), 7.72 (d, 2H, J=4.8Hz), 4.10(s, 3H), 4.07(t, 2H), 1.90–1.70(m, 2H), 0.90(t, 3H) |
| 4 | white needles | 170.2–171.8 (Acetonitril-Ether) | $C_{15}H_{15}N_7O.0.8C_2H_3N$<br>C H N<br>58.29 4.88 32.18<br>58.27 5.13 31.93 | 1715, 1650 | — | (DMSO-$d_6$) 8.87(brs, 1H), 8.70(brs, 1H), 8.14(s, 1H), 8.11(s, 1H), 7.55 (dd, 1H), 4.10(s, 3H), 4.06(t, 2H), 1.85–1.65 (m, 2H), 0.90(t, 3H) |
| 5 | white needles | 243.5–248.5 (Ethanol) | $C_{14}H_{14}N_6O_2$<br>C H N<br>56.51 4.93 27.95<br>56.37 4.73 28.17 | 1712, 1651 | — | ($CDCl_3$) 7.67(dd, 1H), 7.61(s, 1H), 7.39(dd, 1H), 6.59(dd, 1H), 4.22 (t, 2H), 4.19(s, 3H), 2.00–1.80(m, 2H), 1.02 (t, 3H) |
| 6 | white needles | 178.7–179.1 (Isopropanol) | $C_{15}H_{16}N_6O_2$<br>C H N<br>57.36 5.03 26.93<br>57.68 5.16 26.91 | 1709, 1656 | — | ($CDCl_3$) 7.60(s, 1H), 7.39(d, 1H, J=2.0Hz), 6.71(d, 1H, J=2.0Hz), 4.20(t, 2H), 4.19(s, 3H), 2.52(s, 3H), 1.93–1.75 (m, 2H), 1.00(t, 3H) |
| 7 | light yellow powder | 164.4–165.1 (Isopropanol) | $C_{17}H_{18}N_6O_2$<br>C H N<br>60.18 5.21 24.82<br>60.34 5.36 24.84 | 1716, 1650, 1473, 1450 | — | ($CDCl_3$) 7.59(s, 1H), 7.53–7.47(m, 2H), 7.10–6.97(m, 2H), 4.19(s, 3H), 4.15(t, 3H), 3.76(s, 3H), 1.93–1.77(m, 2H), 0.99(t, 3H) |
| 8 | white needles | 165.4–166.8 (Toluene) | $C_{17}H_{18}N_6O_2$<br>C H N<br>60.18 5.40 24.54<br>60.34 5.36 24.84 | 1722, 1649, 1570, 1449 | — | ($CDCl_3$) 7.61(s, 1H), 7.43–7.26(m, 3H), 7.08–7.03 (m, 1H), 4.20(s, 3H), 4.22–4.16(m, 2H), 3.86(s, 3H), 1.95–1.75(m, 2H), 0.98(t, 3H) |
| 9 | white needles | 161.0–163.3 (Toluene-Cyclohexane) | $C_{17}H_{18}N_6O_2$<br>C H N<br>60.55 5.49 25.24<br>60.34 5.36 24.84 | 3105, 2960, 1715, 1650, 1483 | — | (DMSO-$d_6$) 8.07(s, 1H), 7.64(d, 2H, J=6.8Hz), 7.03 (d, 2H, J=6.8Hz), 4.08(s, 3H), 4.04(t, 2H), 3.84(s, 3H), 1.80–1.60(m, 2H), 0.89(t, 3H) |
| 10 | white needles | 163.4–165.2 (Toluene-Cyclohexane) | $C_{16}H_{15}N_6OCl$<br>C H N<br>56.19 4.28 24.42<br>56.06 4.41 24.52 | 1721, 1649, 1567, 1449, 1436 | — | (DMSO-$d_6$) 8.12(s, 1H), 7.65–7.45(m, 4H), 4.10(s, 3H), 4.03(t, 2H), 1.80–1.60(s, 2H), 0.87(t, 3H) |
| 11 | white needles | 142.9–143.8 (Ethanol) | $C_{16}H_{16}N_6OCl$<br>C H N<br>56.40 4.23 24.63<br>56.06 4.41 24.52 | 1708, 1659, 1447, 1299 | — | ($CDCl_3$) 7.78–7.77(m, 1H), 7.66–7.62(m, 1H), 7.62(s, 1H), 7.51–7.39(m, 2H), 4.21(s, 3H), 4.20(t, 2H), 1.95–1.75(m, 2H), 0.99 (t, 3H) |

TABLE 9-continued

| Compound No. | Properties | Melting point (°C.) (Recrystallization solvent) | Elemental analysis (%) (upper: found lower: calcd.) | IR (KBr) $cm^{-1}$ | MS (m/e) Relative intensity | $^1H$-NMR (Measuring solvent) δ (ppm) |
|---|---|---|---|---|---|---|
| 12 | white needles | 175.1-177.0 (Toluene-Cyclohexane) | $C_{16}H_{15}N_6OCl$<br>C H N<br>55.79 4.45 24.70<br>56.06 4.41 24.52 | 1728, 1657, 1470, 1450 | — | ($DMSO-d_6$) 8.09(s, 1H), 7.73(d, 2H, J=7.5Hz), 7.56 (d, 2H, J=7.5Hz), 4.09(s, 3H), 4.05(t, 2H), 1.85-1.65(m, 2H), 0.89(t, 3H) |
| 13 | light yellow powder | 177.1-177.8 (Ethanol-water) | $C_{16}H_{17}N_7O$<br>C H N<br>59.10 5.47 30.67<br>59.43 5.30 30.32 | 3420, 3350, 1710, 1655, 1448 | — | ($DMSO-d_6$) 8.06(s, 1H), 7.20-7.05(m, 2H), 6.70 (d, 1H), 6.57(t, 1H), 5.20(brs, 2H), 4.09(s, 3H), 4.00(t, 2H), 1.80-1.60(m, 2H), 0.88(t, 3H) |
| 14 | white needles | 169.9-171.2 | $C_{17}H_{18}N_6O$<br>C H N<br>63.62 5.53 26.39<br>63.34 5.63 26.07 | 1708, 1646, 1478, 1445 | — | ($CDCl_3$) 7.64(d, 2H, J=8.0Hz), 7.60(s, 1H), 7.29(d, 2H, J=8.0Hz), 4.20(s, 3H), 4.19(t, 2H), 2.43(s, 3H), 1.93-1.77 (m, 2H), 0.98(t, 3H) |
| 15 | white needles | 205.8-207.0 (Isopropanol) | $C_{17}H_{15}N_6F_3O$<br>C H N<br>54.0 3.78 22.13<br>54.25 4.02 22.33 | 1707, 1652, 1574, 1450, 1409 | — | ($CDCl_3$) 7.91(d, 2H, J=8.0 Hz), 7.75(d, 2H, J=8.0Hz), 7.64(s, 1H), 4.22(s, 3H), 4.20(t, 2H), 1.97-1.77(m, 2H), 1.00(t, 3H) |
| 16 | white needles | 117.0-117.2 (Toluene) | $C_{16}H_{15}N_7O_3.0.3H_2O$<br>C H N<br>53.56 4.27 27.46<br>53.57 4.38 27.33 | 1707, 1655, 1515, 1449 | — | ($CDCl_3$) 8.35(d, 2H, J=9.0 Hz), 7.98(d, 2H, J=9.0Hz), 7.66(s, 1H), 4.22(s, 3H), 4.21(t, 2H), 1.95-1.77 (m, 2H), 1.00(t, 3H) |
| 17 | light yellow needles | 192.0-193.9 (Ethanol-water) | — | 3400, 1722, 1657, 1482, 1451 | 326($M^+$, 100) 297(12) 284(33) 283(42) 163(12) | ($CDCl_3$) 7.77(dd, 1H, J=6.3, 8.7Hz), 7.61(s, 1H), 7.18(dd, 1H, J=8.7, 8.7Hz), 4.22(t, 2H), 4.20(s, 3H), 1.93-1.75(m, 2H), 0.99 (t, 3H) |
| 18 | white needles | 255.9-256.2 (Isopropanol) | $C_{18}H_{21}N_7O.1/5HCl$<br>C H N<br>60.36 5.89 27.36<br>60.27 5.96 27.33 | 1706, 1651, 1612, 1478, 1449 | — | ($CDCl_3$) 7.73(d, 2H, J=9.0 Hz), 7.59-7.04(brd, 2H), 4.20(s, 3H), 4.19(t, 2H), 3.08(s, 6H), 2.00-1.75 (m, 2H), 0.99(t, 3H) |
| 19 | white needles | 257.3-258.1 (Acetonitril) | $C_{16}H_{14}N_6Cl_2O$<br>C H N<br>50.98 3.54 22.15<br>50.94 3.74 22.28 | 1722, 1650, 1571, 1448 | — | ($CDCl_3$) 7.63(s, 1H), 7.56(m, 1H), 7.45-7.43 (m, 2H), 4.21(s, 3H), 4.17(t, 3H), 1.93-1.75 (m, 2H), 0.97(t, 3H) |
| 20 | white needles | 175.0-176.1 (Ethanol-water) | $C_{16}H_{14}N_6OCl_2.0.6H_2O$<br>C H N<br>49.27 3.69 21.39<br>49.52 3.95 21.66 | 1720, 1650, 1571, 1450 | 378($M^+$ + 2, 66), 376 ($M^+$, 100) 336(22), 335(32), 334(35), 333(37) | ($CDCl_3$) 7.90-7.89(m, 1H), 7.63(s, 1H), 7.64-7.54(m, 2H), 4.20(s, 3H), 4.19 (t, 2H), 1.97-1.78(m, 2H), 1.00(t, 3H) |
| 21 | white powder | 211-215 (Dioxane) | $C_{18}H_{20}N_6O_3$<br>C H N<br>58.46 5.30 23.16<br>58.67 5.48 22.82 | 1723, 1652, 1499, 1447 | — | ($CDCl_3$) 7.60(s, 1H), 7.38-7.33(m, 2H), 6.98 (d, 1H, J=8.2Hz), 4.21(t, 2H), 4.20(s, 3H), 3.95 (s, 3H), 3.94(s, 3H), 1.97-1.78(m, 2H), 0.99 (t, 3H) |
| 22 | white needles | 251.3-252.9 (Toluene) | $C_{18}H_{18}N_6O_3$<br>C H N<br>59.13 5.17 22.82<br>59.01 4.95 22.94 | 1715, 1653, 1611, 1568, 1439 | — | ($DMSO-d_6$) 8.11(s, 1H), 8.06(d, 2H, J=8.5Hz), 7.86(d, 2H, J=8.6Hz), 4.10(s, 3H), 4.05(t, 2H), 3.91(s, 3H), 1.82-1.62 (m, 2H), 0.89(t, 3H) |

EXAMPLE 23

6,9-Dihydro-3-(4-carboxyphenyl)-9-methyl -6-n-propyl-5H-1,2,4-triazolo[3,4-i]purin-5-one (Compound 23)

After 3.00 g (8.20 mmol) of Compound 22 prepared in Example 22 was dissolved in 30 ml of dimethylsulfoxide, 11.7 g (82 mmol) of lithium iodide was added and the mixture was stirred at 140° C. for 13 hours. After cooling, 500 ml of water was added to the solution followed by extraction 10 times with 50 ml of chloroform-methanol (101). The extracts were combined and washed with 0.2 M sodium thiosulfate aqueous solution and with a saturated aqueous sodium chloride solution. After drying over anhydrous magnesium sulfate, the solvent was evaporated under reduced pressure. The residue was purified by silica gel column chromatography (eluent: 10% methanol/chloroform), and triturated with 10 ml of methanol to afford 1.40 g (yield, 49%) of Compound 23 as a light yellow powder.

Melting point: >315° C.

IR (KBr) νmax ($cm^{-1}$): 3400, 1728, 1700, 1650, 1593, 1553.

$^1$H-NMR (DMSO-$d_6$) δ(ppm): 8.09(s, lH), 8.05(d, 2H, J=8.3Hz), 7.74(d, 2H, J=8.3Hz), 4.09(s, 3H), 4.04(t, 2H), 1.82-1.62(m, 2H), 0.89(t, 3H).

MS (m/e: relative intensity): 352(M+, 100), 310(59), 309(79).

EXAMPLE 24

6,9-Dihydro-3,9-dimethyl-6-n-propyl-5H -1,2,4-triazolo[3,4-i]purin-5-one (Compound 24)

After 100 ml of toluene and 1.49 g (20.2 mmol) of acetohydrazide were added to 4.00 g (16.8 mmol) of Compound a prepared in Reference Example 1, the mixture was refluxed for 53 hours under heating. After cooling, the solution was concentrated, 100 ml of chloroform and 50 ml of 50% saturated sodium bicarbonate aqueous solution were added and the aqueous layer was extracted twice with 30 ml of chloroform. The extracts were combined and washed with a saturated aqueous sodium chloride. After drying over anhydrous sodium sulfate, the solvent was evaporated under reduced pressure. The residue was purified by silica gel column chromatography (eluent: 2% methanol/chloroform) to afford 1.39 g (yield, 34%) of Compound 24 as a white powder.

Melting point: 191.9°-193.6° C. (acetonitrile ethanol).

Elemental analysis: as $C_{11}H_{14}N_60.3/4CH_3CN.1/5C_2H_5OH$.

| | | | |
|---|---|---|---|
| Found (%): | C 54.21 | H 5.99 | N 32.84 |
| Calcd. (%): | C 54.12 | H 6.14 | N 33.03 |

IR (KBr) νmax ($cm^{-1}$): 1715, 1655, 1450.

$^1$H-NMR ($CDCl_3$) δ(ppm): 7.57(s, lH), 4.19(t, 2H), 4.14(s, 3H), 2.95(s, 3H), 1.95-1.80(m, 2H), 1.02(t, 3H).

$^{13}$C-NMR ($CDCl_3$) δ(ppm): 149.1, 145.7, 143.1, 142.7, 139.2, 104.2, 45.18, 34.1, 21.3, 13.4, 11.1.

EXAMPLE 25

6,9-Dihydro-3-methyl-6-n-propyl-5H -1,2,4-triazolo[3,4-i]-purin-5-one (Compound 25)

After 5 ml of dimethylsulfoxide and 730 mg (9.82 mmol) of acetohydrazide were added to 2.00 g (8.93 mmol) of Compound b prepared in Reference Example 2, the mixture was stirred at 160° C. for 30 minutes. After cooling, the 200 ml of water and 50 ml of chloroform were added to the solution. After fractionation, the aqueous layer was extracted twice with 50 ml of chloroform. The extracts were combined and washed twice with water and once with a saturated aqueous sodium chloride solution. After drying over anhydrous sodium sulfate, the solvent was evaporated under reduced pressure. The residue was purified by silica gel column chromatography (eluent: 5% methanol/chloroform) to afford 1.16 mg (yield, 52%) of Compound 25 as a white powder.

Melting point: 298.0°-299.2° C. (ethanol).

Elemental analysis: as $C_{10}H_{12}N_6O.0.1H_2O$.

| | | | |
|---|---|---|---|
| Found (%): | C 51.58 | H 5.25 | N 35.62 |
| Calcd. (%): | C 51.32 | H 5.25 | N 35.90 |

IR (KBr) νmax ($cm^{-1}$): 1715, 1662.

$^1$H-NMR (DMSO-$d_6$) δ(ppm): 13.78(brs, lH), 8.01(s, lH), 4.08(t, 2H), 2.76(s, 3H), 1.95-1.70(m, 2H), 0.92(t, 3H).

EXAMPLE 26

8-Cyclopentyl-6,9-dihydro-6-n-propyl-3-phenyl-5H-1,2,4triazolo[3,4-i]purin-5-one (Compound 26)

After 2.00 g (6.85 mmol) of Compound c prepared in Reference Example 3 was dissolved in 50 ml of toluene, 1.40 g (10.28 mmol) of benzoylhydrazine was added to the solution. The mixture was refluxed for 4 hours and a half under heating. After cooling, 100 ml of chloroform was added to the reaction solution. The precipitates were collected by filtration to afford 2.22 g (yield, 86%) of 6-(N'-benzoylhydrazino)-8-cyclopentyl-3,7-dihydro-3-n-propyl-2H-purin-2-one (Compound mc) as a white powder.

Melting point: 223.1°-224.9° C.

Elemental analysis: as $C_{20}H_{24}N_6O_2$.

| | | | |
|---|---|---|---|
| Found (%): | C 63.10 | H 6.30 | N 22.01 |
| Calcd. (%): | C 63.14 | H 6.36 | N 22.09 |

IR (KBr) νmax ($cm^{-1}$): 1680, 1614, 1574, 1504.

$^1$H-NMR (DMSO-$d_6$) δ(ppm): 12.8-12.3(brs, lH), 10.7-10.2(br, 2H), 8.04-7.89(m, 2H), 7.65-7.48(m, 3H), 3.83(t, 2H), 3.30-3.10(m, lH), 2.20-1.60(m, 10H), 0.87(t, 3H).

1.07 g of Compound 26 as white needles was obtained from 1.89 g (4.97 mmol) of the Compound mc by similar manner to Example 1 (yield, 59%).

Melting point: 252.9°-254.5° C. (ethanol-water)

Elemental analysis: as $C_{20}H_{22}N_6O$.

| | | | |
|---|---|---|---|
| Found (%): | C 66.54 | H 6.20 | N 23.25 |
| Calcd. (%): | C 66.28 | H 6.12 | N 23.19 |

IR (KBr) νmax ($cm^{-1}$): 1720, 1660.

$^1$H-NMR (DMSO-$d_6$) δ(ppm): 13.55(brs, lH), 7.80-7.60(m, 2H), 7.55-7.40(m, 3H), 4.05(t, 2H), 3.35-3.15(m, lH), 2.15-1.55(m, 10H), 0.89(t, 3H)

EXAMPLE 27

8-Cyclopentyl-6,9-dihydro-3-methyl-6-n-propyl-5H-1,2,4-triazolo[3,4-i]purin-5-one (Compound 27)

The procedure was performed in a manner similar to Example 26 except for using 760 mg (10.28 mmol) of acetohydrazide instead of benzoylhydrazine. Thus, 1.92 g (yield, 88%) of 8-cyclopentyl-6-(N'-acetylhydrazino)-3,7- dihydro-3-n-propyl-2H-purin-2-one (Compound md) was obtained as a white powder.

Melting point: >270° C.

Elemental analysis: as $C_{15}H_{22}N_6O_2$.

| | | | |
|---|---|---|---|
| Found (%): | C 56.25 | H 6.98 | N 26.34 |
| Calcd. (%): | C 56.59 | H 6.97 | N 26.40 |

IR (KBr) νmax ($cm^{-1}$): 1667, 1651, 1539.

1.51 g of Compound 27 as white needles was obtained from 1.84 g (5.79 mmol) of Compound md by a similar manner to Example 1 (yield, 87%).

Melting point 307.6°-309.4° C. (isopropanol).

Elemental analysis: as $C_{15}H_{20}N_6O_1$.

| | | | |
|---|---|---|---|
| Found (%): | C 60.33 | H 6.84 | N 27.65 |
| Calcd. (%): | C 59.98 | H 6.71 | N 27.98 |

IR (KBr) νmax ($cm^{-1}$): 1720, 1660.

$^1$H-NMR (DMSO-$d_6$) δ(ppm): 13.39(brs, lH), 4.04(t, 2H), 3.30-3.10(m, lH), 2.75(s, 3H), 2.10-1.55(m, 10H), 0.91(t, 3H).

EXAMPLE 28

6-Benzyl-6,9-dihydro-9-methyl-3-phenyl-5H-1,2,4-triazolo[3,4-i]purin-5-one (Compound 28)

Using 4.00 g (14.0 mmol) of Compound h in Reference Example 8 and 2.28 g (16.8 mmol) of benzoyl hydrazine, the procedure was carried out in a manner similar to Example 2 to give 2.69 g (yield, 54%) of Compound 28 as light yellow needles.

Melting point: 255.3°-256.9° C. (toluene).

Elemental analysis: as $C_{20}H_{16}N_6O.H_2O$.

| | | | |
|---|---|---|---|
| Found (%): | C 67.22 | H 4.37 | N 23.16 |
| Calcd. (%): | C 67.07 | H 4.56 | N 23.46 |

IR (KBr) νmax ($cm^{-1}$): 1717, 1650, 1567, 1451.

$^1$H-NMR (DMSO-$d_6$) δ(ppm): 8.09(s, lH), 7.72-7.67(m, 2H), 7.56-7.44(m, 3H), 7.40-7.35(m, 2H), 7.34-7.20(m, 3H), 5.28(s, 2H), 4.10(s, 3H).

EXAMPLE 29

6,9-Dihydro-3,6-diphenyl-9-methyl-5H -1,2,4-triazolo[3,4-i]- purin-5-one (Compound 29)

Except that 3.50 g (12.9 mmol) of Compound k in Reference Example 10 and 2.10 g (15.4 mmol) of benzoylhydrazine were used, the procedure was performed in a manner similar to Example 2. Thus, 962 mg (yield, 22%) of Compound 29 was obtained as a white powder.

Melting point: 267.9°-269.7° C. (N,N'-dimethylformamide-water).

Elemental analysis: as $C_{19}H_{14}N_6O$.

| | | | |
|---|---|---|---|
| Found (%): | C 66.35 | H 3.81 | N 24.84 |
| Calcd. (%): | C 66.66 | H 4.12 | N 24.55 |

IR (KBr) νmax ($cm^{-1}$): 1717, 1655, 1429

$^1$H-NMR (DMSO-$d_6$) δ(ppm): 7.97(s, lH), 7.73-7.67(m,2H), 7.57-7.41(m, 8H), 4.11(s, 3H).

EXAMPLE 30

6,9-Dihydro-3-phenyl-6-n-propyl-5H -1,2,4-triazolo[3,4-i]- purin-5-one (Compound 30)

The procedure was performed in a manner similar to Example 2 except for using 8.27 g (24.0 mmol) of Compound f obtained in Reference Example 6 and 3.93 g (28.8 mmol) of benzoylhydrazide. Thus, 6.90 g (yield, 69%) of 8-benzyloxy- methyl-6,9-dihydro-3-phenyl-6-n-propyl-5H-1,2,4-triazolo[3,4-i]purin-5-one (Compound me) was obtained as a light yellow powder.

$^1$H-NMR (90 MHz; $CDCl_3$) δ(ppm): 7.75(s, lH), 7.80-7.65 (m, 2H), 7.60-7.45(m, 3H), 7.24(brs, 5H), 5.93 (s, 2H), 4.78(s, 2H), 4.18(t, 2H), 2.00-1.60(m, 2H), 0.99(t, 3H).

After 6.71 g (16.2 mmol) of the Compound me was suspended in 325 ml of toluene, 32.4 ml of 1 M boron tribromide in methylene chloride was dropwise added to the suspension under ice cooling. The mixture was stirred at room temperature for 2 hours. The reaction mixture was poured onto ice water followed by extraction 3 times with 100 ml of chloroform. The extracts were combined and washed with a saturated aqueous sodium chloride. After drying over anhydrous sodium sulfate, the solvent was evaporated under reduced pressure. The precipitates were collected by filtration and then washed with methanol. The crystals were recrystallized from isopropanol to give 2.52 g (yield, 53%) of Compound 30 as white needles.

Melting point: 272.8°-280.0° C. (acetonitrile).

Elemental analysis: as $C_{15}H_{14}N_6O.0.1H_2O.0.5C_2H_3N$.

| | | | |
|---|---|---|---|
| Found (%): | C 60.69 | H 4.75 | N 28.83 |
| Calcd. (%): | C 60.69 | H 5.00 | N 28.75 |

IR (KBr) νmax ($cm^{-1}$): 1720, 1660.

$^1$H-NMR (DMSO-$d_6$) δ(ppm): 14.10-13.80(brs, lH), 8.11 (s, lH), 7.80-7.70(m, 2H), 7.60-7.45(m, 3H), 4.08 (t, 2H), 1.90-1.70(m, 2H), 0.90(t, 3H).

EXAMPLE 31

6,9-Dihydro-6-n-propyl-3-(4-pyridyl) -5H-1,2,4-triazolo-3,4-i]purin-5-one (Compound 31)

The procedure was performed in a manner similar to Example 2 except for using 4.00 g (11.6 mmol) of Compound f prepared in Reference Example 6 and 1.91 g (14.0 mmol) of isonicotinic hydrazide. Thus, 2.32 g (yield, 48%) of 8-benzyloxymethyl-6,9-dihydro-6-n-propyl-3-(4-pyridyl)-5H-1,2,4-triazolo[3,4-i]purin-5-one(Compound mf) obtained as a yellow powder.

$^1$H-NMR (90 MHz; $CDCl_3$) δ(ppm): 8.73(d, 2H, J=8.9Hz), 7.78(s, lH), 7.69(d, 2H, J=8.9Hz), 7.23(brs, 5H), 5.93(s, 2H), 4.78(s, 2H), 4.20(t, 2H), 2.00-1.65 (m, 2H), 1.01(t, 3H)

1.09 g of Compound 31 as white needles was obtained from 2.10 g of Compound mf by the similar elimination reaction of the protecting group to Example 30 (yield, 3%).

Melting point: >330° C. (DMF-dioxan-water).

Elemental analysis: as $C_{14}H_{13}N_7O.0.8H_2O$.

| | | | |
|---|---|---|---|
| Found (%): | C 32.02 | H 4.51 | N 32.02 |
| Calcd. (%): | C 31.67 | H 4.75 | N 31.66 |

IR (KBr) νmax ($cm^{-1}$): 1732, 1659, 1603, 1568, 1514.

$^1$H-NMR (DMSO-$d_6$) δ(ppm): 14.03(s, lH), 8.71(d, 2H, J=5.5Hz), 8.14(s, lH), 7.73(m, 2H), 4.10(t, 2H), 1.85-1.65(m, 2H), 0.91(t, 3H).

EXAMPLE 32

6,9-Dihydro-6-n-propyl-3-(3-pyridyl) -5H-1,2,4-triazolo[3,4-i]purin-5-one (Compound 32)

The procedure was performed in a manner similar to Example 2 except for using 3.50 g (10.2 mmol) of Compound f prepared in Reference Example 6 and 1.68 g (12.2 mmol) of nicotinic acid hydrazide. Thus, 2.87 g (yield, 53%) of 8-benzyloxymethyl-6,9-dihydro-6-n-propyl-3-(3-pyridyl)-5H -1,2,4-triazolo[3,4-i]purin-5-one (Compound mg) was obtained as a yellow powder.

$^1$H-NMR (90MHz; $CDCl_3$) δ(ppm): 9.05-8.90(m, lH), 8.80-8 65(m, lH), 8.20-7.95(m, lH), 7.77(s, lH), 7.55-7.25(m, lH), 7.23(brs, 5H), 5.93(s, 2H), 4.78(s, 2H), 4.20(t, 2H), 2.05-1.70(m, 2H), 1.01(t, 3H).

503 mg of Compound 32 as white needles was obtained (yield, 28%) from 2.50 g (6.02 mmol) of Compound mg and 4 equivalents of boron tribromide by the similar elimination reaction of the protecting group to Example 30.

Melting point: 277.2°-278.2° C. (dioxan).

IR (KBr) νmax ($cm^{-1}$) 1721, 1654, 1571.

$^1$H-NMR (DMSO-$d_6$) δ(ppm): 14.15-13.80(br, 1H), 8.90 (brs, 1H), 8.71(brs, 1H), 8.18-8.14(m, 1H), 8.12 (s, 1H), 7.56(dd, 1H, J=5.0, 7.5Hz), 4.10(t, 2H), 1.85-1.65(m, 2H), 0.91(t, 3H).

MS (m/e; relative intensity): 285(M+, 100), 253(68).

Elemental analysis: as $C_{14}H_{13}N_7O.0.2H_2O$.

| | | | |
|---|---|---|---|
| Found (%): | C 56.12 | H 4.39 | N 32.82 |
| Calcd (%): | C 56.26 | H 4.52 | N 32.80 |

EXAMPLE 33

6,9-Dihydro-6-n-propyl-3-(2-thienyl) -5H-1,2,4-triazoloz-5-one (Compound 33)

The procedure was performed in a manner similar to Example 2 except for using 4.50 g (13.1 mmol) of Compound f obtained in Reference Example 6 and 2.23 g (15.7 mmol) of 2-thiophenecarboxylic acid hydrazide. Thus 2.87 g (yield, 52%) of 8benzyloxymethyl-6,9-dihydro-6-n-propyl-3-(2-thienyl)-5H-1,2,4-triazolo[3,4-i]purin-5-one (Compound mh) was obtained as a light red powder.

$^1$H-NMR (90 MHz; $CDCl_3$) δ(ppm): 8.05-7.90(m, 1H), 7.74 (s, 1H), 7.60-7.45(m, 1H), 7.35-7.05(m, 6H), 5.92(s, 2H), 4.77(s, 2H), 4.21(t, 2H), 2.05-1.65 (m, 2H), 1.03(t, 3H).

1.63 g of Compound 33 as white needles was obtained from 2.65 g (6.31 mmol) of Compound mh by the similar elimination reaction of the protecting group to Example 30 (yield, 87%).

Melting point: 286.8°-290.9° C. (N,N-dimethylformamide-water).

Elemental analysis: as $C_{13}H_{12}N_6OS$.

| | | | |
|---|---|---|---|
| Found (%): | C 52.18 | H 3.74 | N 28.02 |
| Calcd. (%): | C 51.99 | H 4.03 | N 27.98 |

IR (KBr) νmax ($cm^{-1}$): 1721, 1660.

$^1$H-NMR (DMSO-$d_6$) δ(ppm): 13.93(brs, 1H), 8.08(s, 1H), 7.93(dd, 1H, J=1.2, 3.6Hz), 7.76(dd, 1H, J=1.2, 5.2Hz), 7.19(dd, 1H, J=3.6, 5.2Hz), 4.13(t, 2H), 1.90-1.70(m, 2H), 0.93(t, 3H).

EXAMPLE 34

6-Benzyl-6,9-dihydro-3-(4-pyridyl)-5H-1,2,4-triazolo[3,4-i]- purin-5-one (Compound 34)

The procedure was carried out in a manner similar to Example 31 except for using 3.50 g (8.90 mmol) of Compound m obtained in Reference Example 11 instead of Compound f. Thus, 1.06 g (yield, 36%) of Compound 34 (free form) was obtained as a light yellow powder. The powder was suspended in 10 ml of methanol and 1 ml of hydrogen chloride-saturated methanol solution was added to the suspension. The precipitates were collected by filtration to afford 560 mg (yield, 45%) of the hydrochloride of Compound 34 as a yellow powder.

Melting point: >290° C.

IR (KBr) νmax ($cm^{-1}$): 1712, 1655, 1631.

$^1$H-NMR (90 MHz; DMSO-$d_6$) δ(ppm): 9.10-8.75(br, 2H), 8.20-8.05(m, 2H), 8.14(s, 1H), 7.50-7.10(m, 5H), 5.23(s, 2H).

MS (m/e; relative intensity): 343(M+, 76), 91(100).

EXAMPLE 35

6,9-Dihydro-6,9-di-n-propyl-3-phenyl -5H-1,2,4-triazolo [3,4-i]purin-5-one (Compound 35)

After 500 mg (1.70 mmol) of Compound 30 obtained in Example 30 was dissolved in 5 ml of N,N'-dimethylformamide, 81.6 mg (2.04 mmol) of 60% sodium hydride was added to the solution at 0° C. 15 minutes after, 0.25 ml (2.51 mmol) of propyl iodide was added to the reaction solution at 0° C. The solution was stirred at room temperature for 30 minutes. After 20 ml of saturated ammonium chloride was added to the reaction solution at 0° C., the mixture was extracted 3 times with 30 ml of chloroform. The extracts were combined and washed with a saturated sodium chloride aqueous solution. After drying over anhydrous sodium sulfate, the solvent was eva.oprated under reduced pressure. The residue was purified by silica gel column chromatography (eluting solvent: 2% methanol/chloroform) to afford 434 mg (yield, 76%) of Compound 35 as white needles.

Melting point: 215.1°-216.8° C. (ethanol).

Elemental analysis: as $C_{18}H_{20}N_6O$.

| | | | |
|---|---|---|---|
| Found (%): | C 64.10 | H 6.08 | N 25.08 |
| Calcd. (%): | C 64.27 | H 5.99 | N 24.98 |

IR (KBr) νmax ($cm^{-1}$): 1710, 1651.

$^1$H-NMR (DMSO-$d_6$) δ(ppm): 8.15(s, 1H), 7.73-7.66(m, 2H), 7.53-7.40(m, 3H), 4.39(t, 2H), 4.06(t, 2H), 2.10-1.95(m, 2H), 1.83-1.66(m, 2H), 0.91(t, 3H), 0.90(t, 3H).

EXAMPLE 36

6,9-Dihydro-9-methyl-6-n-propyl-5H-1,2,4-triazolo[3,4-i]- purin-5-one (Compound 36)

After 15 ml of ethyl orthoformate was added to 800 mg (3.60 mmol) of Compound n prepared in Reference Example 12, the mixture was refluxed for 2 hours under heating. After the reaction solution was allowed to stand over day and night, the precipitates were collected by filtration to give 760 mg (yield, 91%) of Compound 36 as a light red plate.

Melting point: 217.8°-218.2° C.

IR (KBr) νmax ($cm^{-1}$): 1696, 1649.

$^1$H-NMR (DMSO-$d_6$) δ(ppm): 9.16(s, 1H), 8.02(s, 1H), 4.10(t, 2H), 4.04(s, 3H), 2.00-1.55(m, 2H), 0.92(t, 3H).

MS (m/e: relative intensity): 232(M+, 48), 190(84), 189(100).

EXAMPLE 37

6-Benzyl-6,9-dihydro-3-methyl-5H-1,2,4-triazolo[3,4-i]- purin-5-one (Compound 37)

The procedure was performed in a manner similar to Example 25 except for using 2.20 g (8.08 mmol) of Compound i prepared in Reference Example 8. Thus, 1.40 g (yield, 62%) of Compound 37 was obtained as a light yellow powder.

Melting point: 308.9°-310.3° C.

Elemental analysis: as $C_{14}H_{12}N_6O.0.2H_2O$.

| | | | |
|---|---|---|---|
| Found (%): | C 59.17 | H 3.99 | N 30.01 |

-continued

| | | | |
|---|---|---|---|
| Calcd. (%): | C 59.23 | H 4.40 | N 29.60 |

IR (KBr) νmax ($cm^{-1}$): 1720, 1659.

$^1$H-NMR (DMSO-$d_6$) δ(ppm): 13.83(brs, 1H), 8.03(s, 1H), 7.45–7.20(m, 5H), 5.30(s, 2H), 2.76(s, 3H).

EXAMPLE 38

6-n-Butyl-6,9-dihydro-3-(4-pyridyl)-5H-1,2,4-triazo [3,4-i]purin-5-one (Compound 38)

The procedure was performed in a manner similar to Example 2 except for using 5.61 g (15.7 mmol) of Compound r prepared in Reference Example 16 and 2.36 g (17.2 mmol) of isonicotinic hydrazide. Thus, 4.42 g of (yield, 66%) of 8-benzyloxymethyl-6-n-butyl-6,9-dihydro -3-(4-pyridyl)-5H-1,2,4-triazolo[3,4-i]purin-5-one (Compound mi) was obtained as a yellow powder.

$^1$H-NMR (90 MHz; $CDCl_3$) δ(ppm): 8.71(d, 2H, J=8.8Hz), 7.78(s, 1H), 7.68(d, 2H, J=8.8Hz), 7.22(brs, 5H), 5.93(s, 2H), 4.77(s, 2H), 4.22(t, 2H), 2.00–1.25 (m, 4H), 0.98(t, 3H).

2.82 g of Compound 38 as white needles was obtained (yield, 89%) from 4.42 g of Compound mi by the similar elimination reaction of the protecting group to in Example 30.

Melting point: 271.0°–272.3° C. (isopropanol)

Elemental analysis: as $C_{15}H_{15}N_7O$.

| | | | |
|---|---|---|---|
| Found (%): | C 58.13 | H 4.97 | N 31.49 |
| Calcd. (%): | C 58.24 | H 4.89 | N 31.70 |

IR (KBr) νmax ($cm^{-1}$): 1718, 1654.

$^1$H-NMR (DMSO-$d_6$) δ(ppm): 13.95(brs, 1H), 8.70(d, 2H,
J=5.6Hz), 8.12(s, 1H), 7.72(d, 2H, J=5.6Hz), 4.11(t, 2H), 1.80–1.65(m, 2H), 1.45–1.30(m, 2H), 0.89(t, 3H).

EXAMPLE 39

9-Benzyl-6,9-dihydro-6-n-propyl-3-(4-pyridyl)-5H-1,2,4triazolo[3,4-i]purin-5-one (Compound 39)

Except that 7.00 g (17.9 mmol) of Compound s obtained in Reference Example 17 and 2.71 g (19.7 mmol) of isonicotinic hydrazide were used, the procedure was performed in a manner similar to Example 2. Thus, 4.29 g of (yield, 62%) of Compound 39 was obtained as light yellow needles.

Melting point: 210.2°–211.8° C. (acetonitrile).

Elemental analysis: as $C_{21}H_{19}N_7O.0.1H_2O$.

| | | | |
|---|---|---|---|
| Found (%): | C 65.31 | H 4.87 | N 24.92 |
| Calcd. (%): | C 65.14 | H 5.00 | N 25.32 |

IR (KBr) νmax ($cm^{-1}$): 1728, 1714, 1641.

$^1$H-NMR (DMSO-$d_6$) δ(ppm): 8.70(d, 1H, J=5.8Hz), 8.36 (s, 1H), 7.72(d, 1H, J=5.8Hz), 7.55–7.50(m, 2H), 7.40–7.25(m, 3H), 5.68(s, 2H), 4.06(t, 2H), 1.85–1.65(m, 2H), 0.90(t, 3H).

EXAMPLE 40

6,9-Dihydro-6,9-di-n-propyl-3-(4-pyridyl)-5H-1,2,4-triazolo[3,4-i]purin-5-one (Compound 40)

Except that 2.50 g (8.50 mmol) of Compound t in Reference Example 18 and 1.40 g (10.2 mmol) of isonicotinic hydrazide were used, the procedure was performed in a manner similar to Example 2. Thus, 2.38 g of (yield, 83%) of Compound 40 (free form) was obtained as light yellow needles.

Melting point: 198.0°–200.1° C. (isopropanol)

Elemental analysis: as $C_{17}H_{19}N_7O$.

| | | | |
|---|---|---|---|
| Found (%): | C 60.29 | H 5.80 | N 29.30 |
| Calcd. (%): | C 60.52 | H 5.68 | N 29.06 |

IR (KBr) νmax ($cm^{-1}$): 1715, 1647.

NMR ($CDCl_3$) δ(ppm): 8.76(d, 2H, J=5.2Hz), 7.72(d, 2H, J=5.2Hz), 7.66(s, 1H), 4.46(t, 2H), 4.24(t, 2H), 2.20–2.08(m, 2H), 1.98–1.80(m, 2H), 1.05–0.98(m, 6H).

After 2.00 g (5.93 mmol) of free form of Compound 40 was suspended in 20 ml of methanol, 5 ml of hydrochloridesaturated ethanol was added to the suspension. The suspension was stirred for 10 minutes, and the solvent was evaporated under reduced pressure. Recrystallization from ethanol gave 1.48 g of Compound 40 (yield, 67%) as yellow needles.

Melting point: 193.8°–199.0° C.

Elemental analysis: as $C_{17}H_{19}N_7O.HCl$.

| | | | |
|---|---|---|---|
| Found (%): | C 54.71 | H 5.64 | N 26.50 |
| Calcd. (%): | C 54.62 | H 5.39 | N 26.23 |

IR (KBr) νmax ($cm^{-1}$): 1710, 1652, 1632, 1592.

$^1$H-NMR ($CDCl_3$) δ(ppm): 8.86(d, 2H, J=6.9Hz), 8.50(d, 2H, J=6.9Hz), 7.76(s, 1H), 4.49(d, 2H), 4.29(d, 2H), 2.20–1.80(m, 4H), 1.05–0.95(m, 6H).

EXAMPLE 41

9-Methyl-6-n-propyl-2,5,6,9-tetrahydro-3H-1,2,4-triazolo[3,4-i]purin-3,5-dione (Compound 41)

After 24 ml of dimethylsulfoxide and 1.23 g (11.8 mmol) of ethyl carbazate were added to 2.35 g (9.87 mmol) of Compound a prepared in Reference Example 1, the mixture was stirred at 160° C. for 2 hours. After cooling, 200 ml of water was added to the mixture. The precipitates were collected by filtration and recrystallized from ethanol to afford 1.10 g (yield, 45%) of Compound 41 as a white powder.

Melting point: 299.3°–301.1° C. (ethanol).

Elemental analysis: as $C_{10}H_{12}N_6O_2$.

| | | | |
|---|---|---|---|
| Found (%): | C 48.21 | H 4.73 | N 33.92 |
| Calcd. (%): | C 48.38 | H 4.87 | N 33.85 |

IR (KBr) νmax ($cm^{-1}$): 1757, 1653.

$^1$H-NMR (DMSO-$d_6$) δ(ppm): 11.99(s, 1H), 7.91(s, 1H), 3.90(t, 2H), 3.86(s, 3H), 1.80–1.60(m, 2H), 0.87 (t, 3H).

EXAMPLE 42

6-Benzyl-9-methyl-2,5,6,9-tetrahydro-3H-1,2,4-triazolo[3,4-i]purin-3,5-dione (Compound 42)

The procedure was performed in a manner similar to Example 41 except for using 2.0 g (7.0 mmol) of Compound h prepared in Reference Example 8 and 870 mg (8.4 mmol) of ethyl carbazate. Thus, 1.83 g (yield, 80%) of Compound 42 was obtained as light yellow needles.

Melting point: 295° C. (dioxane-water).

Elemental analysis: as $C_{14}H_{12}N_6O_2$.

| | | | |
|---|---|---|---|
| Found (%): | C 56.51 | H 3.79 | N 28.47 |

-continued

| | | | |
|---|---|---|---|
| Calcd. (%): | C 56.74 | H 4.09 | N 28.37 |

IR (KBr) νmax ($cm^{-1}$): 1772, 1760, 1694, 1640.

$^1$H-NMR (DMSO-$d_6$) δ(ppm): 11.99(brs, lH), 7.90(s, lH), 7.42-7.25(m, 5H), 5.13(s, 2H), 3.87(s, 3H).

EXAMPLE 43

8-Cyclopentyl-6-n-propyl-2,5,6,9-tetrahydro-3H-1,2,4triazolo[3,4-i]purin-3,5-dione (Compound 43)

The procedure was performed in a manner similar to Example 41 except for using 1.50 g (5.14 mmol) of Compound e obtained in Reference Example 5 and 640 mg (6.17 mmol) of ethyl carbazate. Thus, 571 mg (yield, 37%) of Compound 43 was obtained as white needles.

Melting point: 297.1°-298.8° C. (dioxane-water).

Elemental analysis: as $C_{14}H_{18}N_6O_2.0.1C_4H_8O_2$.

| | | | |
|---|---|---|---|
| Found (%): | C 55.27 | H 6.08 | N 26.82 |
| Calcd. (%): | C 55.59 | H 6.09 | N 27.01 |

IR (KBr) νmax ($cm^{-1}$): 1751, 1694, 1654.

$^1$H-NMR (DMSO-$d_6$) δ(ppm): 13.09(brs, lH), 11.81(s, lH), 3.91(t, 2H), 3.27-3.13(m, lH), 2.10-1.60(m, 10H), 0.89(t, 3H).

EXAMPLE 44

6,9-Di-n-propyl-2,5,6,9-tetrahydro-3H-1,2,4-triazolo[3,4-i]purin-3,5-dione (Compound 44)

The procedure was performed in a manner similar to Example 41 except for using 1.88 g (7.07 mmol) of Compound o prepared in Reference Example 13 and 0.880 g (8.48 mmol) of ethyl carbazate. Thus, 1.65 g (yield, 85%) of Compound 44 was obtained as white needles.

Melting point: 216.7°-218.0° C. (isopropanol).

Elemental analysis: as $C_{12}H_{16}N_6O_2.0.1C_3H_8O$.

| | | | |
|---|---|---|---|
| Found (%): | C 52.34 | H 5.84 | N 29.91 |
| Calcd. (%): | C 52.33 | H 6.00 | N 29.77 |

IR (KBr) νmax ($cm^{-1}$): 1768, 1647.

$^1$H-NMR ($CDCl_3$) δ(ppm): 10.85(brs, lH), 7.51(s, lH), 4.17(t, 2H), 4.10(t, 2H), 2.05-1.80(m, 4H), 1.00(t, 3H), 0.98(t, 3H).

EXAMPLE 45

6-n-Propyl-2,5,6,9-tetrahydro-3H-1,2,4-triazolo[3,4-i]- purin-3,5-dione (Compound 45)

The procedure was performed in a manner similar to Example 41 except for using 3.98 g (11.6 mmol) of Compound f obtained in Reference Example 6 and 1.45 g (13.9 mmol) of ethyl carbazate. Thus, 1.05 g (yield, 19%) of 2,9-dibenzyloxymethyl-6-n-propyl-2,5,6,9-tetrahydro -3H-1,2,4-triazolo[3,4-i]purin-3.5-dione (Compound mj) was obtained as a light yellow powder.

Melting point: 88.9°-90.3° C.

IR (KBr) νmax ($cm^{-1}$): 1764, 1700, 1653.

$^1$H-NMR ($CDCl_3$) δ(ppm): 7.57(s, lH), 7.40-7.10(m, 10H), 5.66(s, 2H), 5.33(s, 2H), 4.69(s-like, 4H), 4.05 (t, 2H), 2.00-1.60(m, 2H), 1.00(t, 3H)

MS (m/e: relative intensity): 474($M^+$, 28), 414(35), 225(7), 91(100).

After 739 mg (1.56 mmol) of Compound mj was suspended in 40 ml of toluene, 4.18 ml (4.18 mmol) of a solution of 1 M boron tribromide/methylene chloride was dropwise added to the suspension at −78° C. The mixture was stirred at 0° C. for an hour. The mixture was poured onto ice water. 2 N sodium hydroxide aqueous solution was added to adjust to pH 7.5. The mixture was washed 3 times with chloroform. After the aqueous layer was concentrated under reduced pressure, the residue was purified by 200 ml of DIAION HP-40 (manufactured by Mitsubishi Chemical Industry Co., Ltd.) to give 312 mg (yield, 85%) of Compound 45 as white needles.

Melting point: >290° C. (dioxane-water).

Elemental analysis: as $C_9H_{10}N_6O_2.0.1C_4H_8O_2$.

| | | | |
|---|---|---|---|
| Found (%): | C 46.36 | H 4.23 | N 34.51 |
| Calcd. (%): | C 46.46 | H 4.48 | N 34.58 |

IR (KBr) νmax ($cm^{-1}$): 1744, 1700, 1649.

$^1$H-NMR (DMSO-$d_6$) δ(ppm): 13.52(brs, lH), 11.87(s, lH), 7.92(s, lH), 3.94(t, 2H), 1.80-1.60(m, 2H), 0.90(t, 3H).

EXAMPLE 46

9-Methyl-6-n-propyl-2,3,6,9-tetrahydro-3-thioxo-5H-1,2,4triazolo[3,4-i]purin-5-one (Compound 46)

After 800 mg (3.60 mmol) of Compound n prepared in Reference Example 12 was dissolved in 36 ml of pyridine, 3.6 ml of carbon disulfide was added to the solution. The mixture was refluxed for 1.5 hours under heating. After the solvent was evaporated under reduced pressure, 50 ml of toluene was added to the residue. The solvent was reevaporated under reduced pressure, and the residue was tritulated with ether. Recrystallization from acetic acid gave 920 mg (yield, 97%) of Compound 46 as light yellow needles.

Melting point: 275.1°-276.8° C.

Elemental analysis: as $C_{10}H_{12}N_6$/ OS.0.5C $_2H_4O_2$.

| | | | |
|---|---|---|---|
| Found (%): | C 44.87 | H 4.63 | N 28.52 |
| Calcd. (%): | C 44.89 | H 4.79 | N 28.55 |

IR (KBr) νmax ($cm^{-1}$): 1726, 1668.

$^1$H-NMR (DMSO-$d_6$) δ(ppm): s, lH), 7.93(s, lH), 3.93(t, 2H), 3.89(s, 3H), 2.00-1.45(m, 2H), 0.90 (t, 3H).

EXAMPLE 47

6-Benzyl-9-methyl-2,3,6,9-tetrahydro-3-thioxo-5H-1,2,4-triazolo[3,4-i]purin-5-one (Compound 47)

The procedure was performed in a manner similar to Example 46 except for using 1.50 g (5.56 mmol) of Compound p prepared in Reference Example 14. Thus, 1.14 g (yield, 66%) of Compound 47 was obtained as a light yellow powders.

Melting point: 277.5°-278.4° C. (dioxane).

Elemental analysis: as $C_{14}H_{12}N_6OS.0.4C_4H_8O_2.0.3H_2O$.

| | | | |
|---|---|---|---|
| Found (%): | C 53.11 | H 4.10 | N 23.81 |
| Calcd. (%): | C 53.08 | H 4.51 | N 23.81 |

IR (KBr) νmax ($cm^{-1}$): 1730, 1673.

$^1$H-NMR (DMSO-$d_6$) δ(ppm): 7.96(brs, lH), 7.50-7.15(m, 5H), 5.17(s, 2H), 3.90(s, 3H).

MS (m/e: relative intensity): 312($M^+$,53), 91(100).

EXAMPLE 48

2-Ethyl-9-methyl-6-n-propyl-2,5,6,9-tetrahydro-3H-1,2,4-triazolo[3,4-i]purin-2,5-dione (Compound 48)

After 1.60 g (6.45 mmol) of Compound 41 prepared in Example 41 was dissolved in 16 ml of N,N-dimethylformamide, 310 mg (7.74 mmol) of 60% sodium hydride was added to the solution under ice cooling. The mixture was stirred for 10 minutes. After 1.55 ml (19.4 mmol) of ethyl iodide was added under ice cooling, the mixture was stirred at 60° C. for 30 minutes. After concentration of the solution, 50 ml of water was added and the mixture was extracted 3 times with 30 ml of chloroform. The extracts were combined and washed with a saturated aqueous sodium chloride solution. After drying over anhydrous sodium sulfate, the solvent was evaporated under reduced pressure. The residue was purified by silica gel column chromatography (eluting solvent: 3% methanol/chloroform) and recrystallized from toluene to give 820 mg (yield, 46%) of Compound 48 as light yellow needles.

Melting point: 238.1°-239.7° C. (toluene).

Elemental analysis: as $C_{12}H_{16}N_6O_2.0.1H_2O$.

| | | | |
|---|---|---|---|
| Found (%): | C 51.74 | H 5.74 | N 30.21 |
| Calcd. (%): | C 51.83 | H 5.87 | N 30.22 |

IR (KBr) $\nu$max ($cm^{-1}$): 1746, 1696, 1650, 1413.

$^1$H-NMR (DMSO-$d_6$) $\delta$(ppm): 7.92(s, 1H), 3.91(t, 2H), 3.88(s, 3H), 3.78(q, 2H), 1.78-1.62(m, 2H), 1.26 (t, 3H), 0.89(t, 3H).

EXAMPLE 49

6-Benzyl-2-ethyl-9-methyl-2,5,6,9-tetrahydro-3H-1,2,4-triazolo[3,4-i]purin-2,5-dione (Compound 49)

The procedure was performed in a manner similar to Example 48 except for using 1.20 g (4.05 mmol) of Compound 42 obtained in Example 42. Thus, 1.32 g (yield, 100%) of Compound 49 was obtained as white needles.

Melting point: 260.0°-261.1° C. (ethanol).

Elemental analysis: as $C_{16}H_{16}N_6O_2.0.2H_2O$.

| | | | |
|---|---|---|---|
| Found (%): | C 58.63 | H 4.95 | N 25.73 |
| Calcd. (%): | C 58.60 | H 5.04 | N 25.63 |

IR (KBr) $\nu$max ($cm^{-1}$): 1771, 1755, 1695, 1650.

$^1$H-NMR ($CDCl_3$) $\delta$(ppm): 7.60-7.10(m, 5H), 7.41(s, 1H), 5.22(s, 2H), 3.90(s, 3H),.3.87(q, 2H), 1.32(t, 3H).

EXAMPLE 50

3-Amino-6,9-dihydro-9-methyl-6-n-propyl-5H-1,2,4-triazolo[3,4-i]purin-5-one (Compound 50)

After 756 mg (3.40 mmol) of Compound n obtained in Reference Example 12 was dissolved in 10 ml of methanol, 400 mg (3.75 mmol) of cyanogen bromide was added to the solution. The mixture was refluxed for 2 hours under heating. After the mixture was neutralized with saturated aqueous sodium bicarbonate solution, the precipitates were collected by filtration and washed with water to afford 670 mg (yield, 80%) of Compound 50 as a light yellow powder.

Melting point: >270° C. (decomposed).

IR (KBr) $\nu$max ($cm^{-1}$): 1698, 1666, 1616, 1323.

$^1$H-NMR (90 MHz; DMSO-$d_6$) $\delta$(ppm): 7.85(s, 1H), 6.63 (brs, 2H), 3.97(t, 2H), 3.93(s, 3H), 2.00-1.50 (m, 2H), 0.91(t, 3H).

MS (m/e; relative intensity): 247($M^+$, 100), 205(64), 204(75), 149(23).

EXAMPLE 51

6-n-Butyl-9-methyl-2,5,6,9-tetrahydro-3H-1,2,4-triazolo3,4-i]purin-3,5-dione (Compound 51)

1.71 g of Compound 51 as a white powder was obtained (yield, 82%) from 2.0 g (7.94 mmol) of Compound u obtained in Reference Example 19 by the similar method to Example 41.

Melting point: 262.1°-264.5° C. (acetic acid).

Elemental analysis: as $C_{11}H_{14}N_6O_2$

| | | | |
|---|---|---|---|
| Found (%): | C 50.40 | H 5.59 | N 32.12 |
| Calcd. (%): | C 50.37 | H 5.38 | N 32.04 |

IR (KBr) $\nu$max ($cm^{-1}$): 1754, 1698, 1652

$^1$H-NMR (DMSO-$d_6$) $\delta$(ppm): 11.95(brs, 1H), 7.90(s, 1H), 3.94(t, 2H), 3.86(s, 3H), 1.75-1.60(m, 2H), 1.40-1.25(m, 2H), 0.90(t, 3H).

REFERENCE EXAMPLE 1

3,7-Dihydro-7-methyl-6-methylthio-3-n-propyl-2H-purin-2-one (Compound a)

In an argon atmosphere, 10.7 g (268 mmol) of 60% sodium hydride was washed with n-hexane 3 times. The solvent was evaporated under reduced pressure and dried. Under ice cooling, 300 ml of N,N'-dimethylformamide was added and a suspension of 28.2 g (134 mmol) of 3-n-propyl6-thioxanthine (Japanese Published Unexamined Patent Application No. 183287/86) in 200 ml of N,N'-dimethylformamide was dropwise added to the mixture. The mixture was incubated for 15 minutes, and 25.1 ml (403 mmol) of methyl iodide was dropwise added. After stirring for 30 minutes, 50 ml of ethanol was added to the mixture followed by concentration. Then 250 ml of water was added to the concentrate. The precipitates were collected by filtration to give 25.9 g (yield, 81%) of Compound a.

Melting point: 224.7°-226.4° C. (acetonitrile).

Elemental analysis: as $C_{10}H_{14}N_4OS$.

| | | | |
|---|---|---|---|
| Found (%): | C 50.30 | H 5.95 | N 23.35 |
| Calcd. (%): | C 50.40 | H 5.92 | N 23.51 |

IR (KBr) $\nu$max ($cm^{-1}$): 1630, 1596, 1557, 1393.

$^1$H-NMR ($CDCl_3$) $\delta$(ppm): 7.53(s, 1H), 4.16(t, 2H), 4.01 (s, 3H), 2.71(s, 3H), 1.95-1.77(m, 2H), 0.98(t, 3H).

$^{13}$C-NMR ($CDCl_3$) $\delta$(ppm): 160.9, 154.7, 151.6, 143.3, 114.3, 45.0, 34.7, 21.2, 12.2, 11.2.

REFERENCE EXAMPLE 2

3,7-Dihydro-6-methylthio-3-n-propyl-2H-purin-2-one (Compound b)

In an argon atmosphere( 9.77 g (244 mmol) of 60% sodium hydride was washed with n-hexane 3 times. The solvent was evaporated under reduced pressure and dried. After 900 ml of N,N'-dimethylformamide was added 57.0 g (271 mmol) of 3-n-propyl-6-thioxanthine (Japanese Published Unexamined Patent Application No. 183287/86) was gently added under ice cooling. 15 minutes after, 15.2 ml (244 mmol) of methyl iodide was dropwise added to the reaction mixture. After stirring for 30 minutes, 50 ml of ethanol was added and the mixture was concentrated under reduced pressure. Then 400 ml of water was added and precipitates were collected by filtration to give 13.9 g (yield, 23%) of Compound b as light yellow powder. The filtrate was extracted 5 times with 200 ml of chloroform. After washing with a saturated aqueous sodium chloride solution, the extract was dried over anhydrous sodium sulfate, the solvent was evaporated under reduced pressure. The residue was purified by silica gel column chromatography (eluent: 10% methanol/chloroform) to give further 16.0 g (yield, 26%) of Compound b as a light yellow powder.

Melting point: 240.8°–242.5° C.

IR (KBr) $\nu$max (cm$^{-1}$): 3400(br), 1600, 1588, 1572, $^1$H-NMR (DMSO-d$_6$) $\delta$(ppm): 13.54(brs, 1H), 8.13(brs, 1H), 3.99(t, 2H), 2.57(s, 3H), 1.80–1.62(m, 2H), 0.88(t, 3H).

$^{13}$C-NMR (DMSO-d$_6$) $\delta$(ppm): 11.0, 11.3, 20.6, 44.4, 112.8(br), 141.9(br), 149.4(br), 153.8, 160.6(br).

MS (m/e; relative intensity): 224(M$^+$, 36), 195(13), 182(100), 135(43).

REFERENCE EXAMPLE 3

8-Cyclopentyl-3-n-propylxanthine (Compound c)

After 30 g (163 mmol) of 5,6-diamino-1-propyl2,4-(1H,3H)-pyrimidinedione (Japanese Published Unexamined Patent Application No. 57517/80) was suspended in 600 ml of N,N'-dimethylformamide, 17.7 ml (163 mmol) of cyclopentanecarboxylic acid, 30.0 g (196 mmol) of hydroxybenztriazole and 50.5 g (245 mmol) of dicyclohexylcarbodiimide were added to the suspension. The mixture was stirred at room temperature overnight. After insoluble materials were filtered off, the filtrate was evaporated under reduced pressure. To the residue was added 600 ml of 4 N sodium hydroxide aqueous solution and the solution was refluxed for 10 minutes under heating. After ice cooling, insoluble materials were filtered off and 50 ml of methanol was added. The resulting mixture was neutralized with conc. hydrochloric acid. The precipitates were collected by filtration to afford 28.3 g (yield, 66%) of Compound c as a white powder.

Melting point: 311.3°–313.1° C. (dimethylformamide).

Elemental analysis: as C$_{13}$H$_{18}$N$_4$O$_2$.

| | | | |
|---|---|---|---|
| Found (%): | C 59.56 | H 6.96 | N 21.69 |
| Calcd. (%): | C 59.52 | H 6.92 | N 21.36 |

IR (KBr) $\nu$max (cm$^{-1}$): 3150, 2880, 1698, 1669.

$^1$H-NMR (DMSO-d$_6$) $\delta$(ppm): 13.05(brs, 1H), 10.94(s, 1H), 3 86(t, 2H), 3.18–3.04(m, 1H), 2.05–1.55(m, 10H), 0.87(t, 3H).

$^{13}$C-NMR (DMSO-d$_6$) $\delta$(ppm): 157.7, 154.3, 150.9, 149.4, 106.5, 43.3, 39.0, 31.9, 25.0, 20.9, 10.9.

REFERENCE EXAMPLE 4

8-Cyclopentyl-3-n-propyl-6-thioxanthine (Compound d):

14.1 g (53.8 mmol) of Compound c obtained in Reference Example 3 and 19.5 g (87.7 mmol) of phosphorous pentasulfide in 280 ml of pyridine was refluxed for 4 hours under heating. The reaction mixture was poured onto 600 ml of ice water and the precipitates werecollected by filtration. The filtrate was concentrated under reduced pressure and the precipitates were taken out by filtration. The collected precipitates were combined and 400 ml of 2 N sodium hydroxide aqueous solution was added to remove insoluble matters. After neutralization with conc. hydrochloric acid, the precipitates were collected by filtration to give crude Compound d. The crude product was recrystallized from ethanol-water to give 13.5 g (yield, 90%) of Compound d as a light yellow plate.

Melting point: 214.3°–215.9° C.

Elemental analysis: as C$_{13}$H$_{18}$N$_4$OS.1/4C $_2$H$_5$OH.

| | | | |
|---|---|---|---|
| Found (%): | C 56.17 | H 6.76 | N 19.44 |
| Calcd. (%): | C 55.93 | H 6.78 | N 19.33 |

IR (KBr) $\nu$max (cm$^{-1}$): 2960, 1663, 1605, 1510, 1403.

$^1$H-NMR (DMSO-d$_6$) $\delta$(ppm): 13.03(brs, 1H), 1204(brs, 1H), 3.90(t, 2H), 3.30–3.10(m, 1H), 2.05–1.55 (m, 10H), 0.87(t, 3H).

$^{13}$C-NMR (DMSO-d$_6$) $\delta$(ppm): 173.3, 161.5, 148.9, 145.7, 118.5, 56.0, 43.8, 38.7, 32.0, 25.2, 20.7, 18.5, 10.9.

REFERENCE EXAMPLE 5

8-Cyclopentyl-3,7-dihydro-6-methylthio-3-n-propyl-2H-purin-one (Compound e)

The procedure was performed in a manner similar to Reference Example 2 except for using 6.00 g (21.6 mmol) of Compound d obtained in Reference Example 4. Thus, 4.70 g (yield, 75%) of Compound e was obtained as light yellow needles.

Melting point: 257.5°–259.2° C.

Elemental analysis: as C$_{14}$H$_{20}$N$_4$OS.

| | | | |
|---|---|---|---|
| Found (%): | C 57.77 | H 7.22 | N 19.36 |
| Calcd. (%): | C 57.51 | H 6.89 | N 19.16 |

IR (KBr) $\nu$max (cm$^{-1}$): 1599, 1580, 1553, 1513.

$^1$H-NMR (90 MHz; CDCl$_3$) $\delta$(ppm): 4.24(t, 2H), 3.53–3.15 (m, 1H), 2.10(s, 3H), 2.50–1.50(m, 10H), 0.95(t, 3H).

REFERENCE EXAMPLE 6

7-Benzyloxymethyl-3,7-dihydro-6-methylthio-3-n-propyl-2H-purin-2-one (Compound f)

After 224 mg (1.0 mmol) of Compound b obtained in Reference Example 2 was dissolved in 2 ml of N,N'-dimethylformamide, 48.0 mg (1.2 mmol) of 60% sodium hydride was added to the mixture under ice cooling. 15 minutes after, 209 $\mu$l (1.5 mmol) of benzyl chloromethyl ether was added to the mixture. The mixture was stirred for an hour, poured onto 10 ml of water, and extracted 3 times with 5 ml of chloroform. After washing with a saturated aqueous sodium chloride solution, the extracts were dried over anhydrous sodium sulfate and the solvent was evaporated under reduced pressure. The residue was triturated with ether to give 223 mg (yield, 65%) of Compound f as a white powder.

Melting point: 166.8°–168.3° C.

Elemental analysis: as C$_{17}$H$_{20}$N$_4$O$_2$S.

| | | | |
|---|---|---|---|
| Found (%): | C 58.99 | H 5.80 | N 16.22 |
| Calcd. (%): | C 59.28 | H 5.85 | N 16.27 |

IR (KBr) $\nu$max (cm$^{-1}$): 1623, 1592, 1556.

$^1$H-NMR (90 MHz; CDCl$_3$) $\delta$(ppm): 7.58(s, 1H), 7.29(s, 5H), 5.61(s, 2H), 4.59(s, 2H), 4.12(t, 2H), 2.70 (s, 3H), 2.00–1.60(m, 2H), 0.99(t, 3H)

MS (m/e; relative intensity): 344(M$^+$, 19), 302(9), 211(10), 181(10), 91(100).

REFERENCE EXAMPLE 7

3-Benzyl-6-thioxanthine (Compound g)

The procedure was performed in a manner similar to Reference Example 4 except for using 31.0 g (128 mmol) of 3-benzylxanthine [Biochemistry, 16, 3316 (1977)]. Thus, 28.7 g (yield, 87%) of Compound g was obtained as a light yellow powder.

Melting point: 261.8°-263.1° C. (DMSO-water).

IR (KBr) νmax ($cm^{-1}$): 1682, 1600, 1560, 1426.

$^1$H-NMR (90 MHz; DMSO-$d_6$) δ(ppm): 13.4(brs, lH), 12.2 (brs, lH), 7.99(s, lH), 7.50-7.05(m, 5H), 5.12 (s, 2H).

REFERENCE EXAMPLE 8

3-Benzyl-3,7-dihydro-7-methyl-6-methylthio-2H-purin-2-one (Compound h) and 3-benzyl-3,7-dihydro-6-methylthio -2H-purin-2-one (Compound i)

The procedure was performed in a manner similar to Reference Example 2 except for using 14 g (54.3 mmol) of Compound g obtained in Reference Example 7. The crude product was purified by silica gel column chromatography and a product was eluted with 5% methanol/chloroform. Concentration of the elution (5% methanol/chloroform) gave 5.86 g (yield, 40%) of Compound h as a light yellow powder.

Melting point: 268.1°-269.8° C .

Elemental analysis: as $C_{13}H_{12}N_4OS$.

| | | | |
|---|---|---|---|
| Found (%): | C 57.42 | H 4.13 | N 20.14 |
| Calcd. (%): | C 57.34 | H 4.44 | N 20.57 |

IR (KBr) νmax ($cm^{-1}$) 3420(br), 1600, 1566, 1543.

$^1$H-NMR (90 MHz; DMSO-$d_6$) δ(ppm): 13.50(brs, lH), 8.07 (s, lH), 7.45-7.05(m, 5H), 5.22(s, 2H), 2.60(s, 3H).

MS (m/e: relative intensity): 272(M+, 53), 257(11), 225(18), 91(100), 65(18),

Concentrating of the elution (2% methanol/-chloroform) fraction eluted by silica gel column chromatography afforded 7.24 g of the residue. The procedure was performed in a manner similar to Reference Example 1 except that 7.24 g of the residue was used. Thus, 5.13 g (yield, 33%) of Compound i was obtained as a light yellow powder.

Melting point: 214.8°-216.4° C.

IR (KBr) νmax ($cm^{-1}$): 1633, 1591. 1558.

$^1$H-NMR (90 MHz; $CDCl_3$) δ(ppm): 7.47(s, lH), 7.60-7.05 (m, 5H), 5.32(s, 2H), 3.82(s, 3H), 2.67(s, 3H).

MS (m/e: relative intensity): 286(M+, 97), 271(40), 228(50), 211(17), 195(19), 91(100).

REFERENCE EXAMPLE 9

3-Phenyl-6-thioxanthine (Compound j)

The procedure was performed in a manner similar to Reference Example 4 except for using 23.8 g (104 mmol) of 3-phenylxanthine [Chem. Pharm. Bull., 14, 1365 (1966)]. Thus, 19.9 g (yield, 78%) of Compound j was obtaiend as a light yellow powder.

Melting point: >290° C.

IR (KBr) νmax ($cm^{-1}$): 1682, 1595, 1587, 1415.

$^1$H-NMR (90 MHz; DMSO-$d_6$) δ(ppm): 7.94(s, lH), 7.60-7.30(m, 5H).

REFERENCE EXAMPLE 10

3,7-Dihydro-7-methyl-6-methylthio-3-phenyl-2H-purin-2-one (Compound k) and 3,7-dihydro-9-methyl-6-methylthio -2H-purin-2-one (Compound l)

The procedure was performed in a manner similar to Reference Example 1 except for using 9.89 g (40.5 mmol) of Compound g obtained in Reference Example 7. The crude product was purified by silica gel column chromatography (eluent: 1% methanol/chloroform). Thus, 7.75 g (yield, 74%) of Compound k and 1.62 g (yield, 16%) of Compound ( were obtained as a light yellow powder.

Physicochemical properties of Compound k are as follows.

Rf: 0.55 [TLC plate: silica gel 60$F_{254}$ (layer thickness of 0.25 mm, manufactured by Merck), developing solvent: 10% methanol/chloroform].

Melting point: 261.1°-262.8° C.

IR (KBr) νmax ($cm^{-1}$) 1640, 1571, 1555.

$^1$H-NMR (90 MHz; $CDCl_3$) δ(ppm): 7.48(s, lH), 7.60-7.30 (m, 5H), 4.01(s, 3H), 2.75(s, 3H).

Physicochemical properties of Compound 1 are as follows.

Rf: 0.46 [TLC plate: silica gel 60$F_{254}$ (layer thickness of 0.25 mm, manufactured by Merck), developing solvent: 10% methanol/chloroform].

IR (KBr) νmax ($cm^{-1}$) 1660, 1556, 1371.

$^1$H-NMR ($CDCl_3$) δ(ppm): 7.62-7.50(m, 3H), 7.45-7.37 (m, 2H), 7.27(s, lH), 2.94(s, 3H), 2.69(s, 3H)

$^{13}$C-NMR ($CDCl_3$) δ(ppm): 171.2, 153.8, 139 6, 138.8, 135.2, 130.1, 130.0, 129.1, 122.2, 33.0, 11.9.

MS (m/e: relative intensity): 272(M+, 96), 225(88), 198(14), 104(17), 77(28), 42(100).

REFERENCE EXAMPLE 11

3-Benzyl-7-benzyloxymethyl-3,7-dihydro-6-methylthio-2H-purin-2-one (Compound m)

The procedure was performed in a manner similar to Reference Example 4 except that 7.00 g (25.7 mmol) of Compound f obtained in Reference Example 6 was used. Thus, 9.15 g (yield, 91%) of Compound m was obtained as a white powder.

Melting point: 193.7°-195.2° C.

IR (KBr) νmax ($cm^{-1}$): 1641, 1625, 1586. 1555.

$^1$H-NMR (90 MHz; $CDCl_3$) δ(ppm): 7.59(s, lH), 7.65-7.15 (m, 10H), 5.60(s, 2H), 5.36(s, 2H), 4.58(s, 2H), 2.69(s, 3H).

REFERENCE EXAMPLE 12

3,7-Dihydro-6-hydrazino-7-methyl-3-n-propyl-2H-purin-2-one (Compound n)

After 50 ml of hydrazine monohydrate was added to 5.00 g (21.0 mmol) of Compound a prepared in Reference Example 1, the mixture was stirred at room temperature for 2 days. The precipitates were collected by filtration and washed with isopropanol to give 4.04 g (yield, 87%) as a white powder.

Melting point: 180.1°-181.9° C.

IR (KBr) νmax ($cm^{-1}$): 1673.

$^1$H-NMR (90 MHz; $CDCl_3$) δ(ppm): 7.25(s, lH), 3.92(t, 2H), 3.87(s, 3H), 2.00-1.55(m, 2H), 0.97(t, 3H).

MS (m/e; relative intensity): 222(M+, 100), 193(13), 180(49), 179(22).

REFERENCE EXAMPLE 13

3,7-Dihydro-3,7-di-n-propyl-6-methylthio-2H-purin-2-one (Compound o)

2.00 g (8.93 mmol) of Compound b obtained in Reference Example 2 was gently added to a suspension of 356 mg (8.93 mmol) of 60% sodium hydride in 20 ml of N,N-dimethylformamide at 0° C. 10 minutes after, 2.64 ml (27.0 mmol) of propyl iodide was gently added to the mixture. The mixture was stirred at room temperature for 2 hours and a half. After 150 ml of saturated ammonium chloride aqueous solution was added to the reaction solution, the mixture was extracted 3 times with chloroform. The extracts were combined and washed twice with a saturated aqueous sodium chloride. After drying over anhydrous sodium sulfate, the solvent was evaporated under reduced pressure. 50% ether/n-hexane was added to the residue. The precipitates were taken out by filtration to give 2.09 g (yield, 84%) of Compound o as a light yellow powder.

$^1$H-NMR ($CDCl_3$) δ(ppm): 7.53(s, 1H), 4.22(t, 2H), 4.14 (t, 2H), 2.70(s, 3H), 2.20–1.65(m, 4H), 1.15–0.90 (m, 6H).

REFERENCE EXAMPLE 14

3-Benzyl-3,7-dihydro-6-hydrazino-7-methyl-2H-purin-2-one (Compound p)

After 16.0 ml of hydrazine hydrate was added to 2.00 g (6.99 mmol) of Compound h prepared in Reference Example 8, the mixture was stirred at room temperature for day and night. The reaction mixture was poured onto 300 ml of water and the precipitates were taken out by filtration and washed with ether to give 1.60 g (yield, 85%) of Compound p as a white powder.

Melting point: 180.0°–181.9° C.

MS (m/e; relative intensity): 222(M+, 100), 180(52)

$^1$H-NMR (DMSO-$d_6$) δ(ppm): 7.78(s, 1H), 7.50–7.10(m, 5H), 5.03(s, 2H), 3.80(s, 3H).

REFERENCE EXAMPLE 15

3-n-Butyl-3,7-dihydro-6-methylthio-2H-purin-2-one (Compound q)

7.88 g of Compound q (yield, 41%) was obtained from 18.2 g (81.0 mmol) of 3-n-butyl-6-thioxanthine (Japanese Published Unexamined Patent Application No. 183287/86, by the similar method to Reference Example 2 as a yellow powder.

Elemental analysis: as $C_{16}H_{14}N_4OS$.

| | | | |
|---|---|---|---|
| Found (%): | C 50.22 | H 6.02 | N 23.67 |
| Calcd. (%): | C 50.40 | H 5.92 | N 23.51 |

NMR (DMSO-$d_6$; 90 MHz) δ(ppm): 8.05(s, 1H), 4.00(t, 2H), 2.56(s, 3H), 1.85–1.05(m, 4H), 0.89(t, 3H)

MS (m/e: relative intensity): 238(M+, 38), 196(100), 182(73), 135(60).

REFERENCE EXAMPLE 16

7-Benzyloxymethyl-3-n-butyl-3,7-dihydro -6-methylthio-2H-purin-2-one (Compound r)

4.83 g of Compound r (yield, 85%) as a white powder was obtained from 3.78 g (15.9 mmol) of Compound q in Reference Example 15, by the method similar to Reference Example 6.

$^1$H-NMR ($CDCl_3$: 90 MHz) δ(ppm): 7.58(s, 1H), 7.28(brs, 5H), 5.60(s, 2H), 4.59(s, 2H), 4.17(t, 2H), 2.70 (s, 3H), 1.90–1.15(m, 4H), 0.95(t, 3H).

MS (m/e: relative intensity): 358(M+, 14), 316(26), 91(100).

REFERENCE EXAMPLE 17

7-Benzyl-6-benzylthio-3,7-dihydro-3-n-propyl-2H-purin-2-one (Compound s)

8.30 g of Compound s (yield, 89%) as a white powder was obtained from 5.00 g (23.8 mmol) of 3-n-propyl-6-thioxanthine (Japanese Published Unexamined Patent Application No. 183287/86) and 7.08 ml (59.5 mmol) of benzyl bromides, by the similar manner to Reference Example 1.

$^1$H-NMR ($CDCl_3$; 90 MHz) δ(ppm): 7.48(s, 1H), 7.50–7.00(m, 10H), 5.41(s, 2H), 4.60(s, 2H), 4.16 (t, 2H), 2.05–1.60(m, 2H;, 1.00(t, 3H).

REFERENCE EXAMPLE 18

3,7-Dihydro-3,7-di-n-propyl-6-n-propylthio-2H-purin-2-one (Compound t)

3.15 g of Compound t (yield, 75%) as a light yellow powder was obtained from 3.00 g (14.3 mmol) of 3-n-propyl-6-thioxanthine (Japanese Published Unexamined Patent Application No. 183287/86) and 3.49 ml (35.7 mmol) of propyliodide, by similar manner to Reference Example 1.

$^1$H-NMR ($CDCl_3$; 90 MHz) δ(ppm): 7.55(s, 1H), 4.30–4.00 (m, 4H), 3.38(t, 2H), 2.15–1.55(m, 6H), 1.20–0.85(m, 9H).

REFERENCE EXAMPLE 19

3-n-Butyl-3,7-dihydro-7-methyl-6-methylthio-2H-purin-2-one (Compound u)

6.33 g of Compound u (yield, 52%) as a light yellow powder was obtained from 10.7 g (47.9 mmol) of 3-n-butyl-6-thioxanthine (Japanese Published Unexamined Patent Application No. 183287/86), by the similar method to Reference Example 1.

$^1$H-NMR ($CDCl_3$; 90 MHz) δ(ppm): 7.50(s, 1H), 4.18(t, 2H), 3.98(s, 3H), 2.68(s, 3H), 1.95–1.20(m, 4H), 0.93(t, 3H).

MS (m/e; relative intensity): 252(M+,38), 210(100), 96(68).

Pharmaceutical preparation 1

Tablet:
A tablet having the following composition was prepared according to the conventional method.

| | |
|---|---|
| Compound 25 | 20 mg |
| Lactose | 60 mg |
| Potato starch | 30 mg |
| Polyvinyl alcohol | 3 mg |
| Magnesium stearate | 1 mg |

Pharmaceutical preparation 2

Powder:
A powder having the following composition was prepared according to the conventional method.

| | |
|---|---|
| Compound 31 | 20 mg |
| Lacrose | 300 mg |

Pharmaceutical preparation 3

Syrup:
A syrup having the following composition was prepared according to the conventional method.

| | |
|---|---|
| Compound 41 | 20 mg |
| Refined saccharose | 30 mg |
| Ethyl p-hydroxybenzoate | 40 mg |
| Propyl p-hydroxybenzoate | 10 mg |
| Strawberry flavor | 0.1 ml |
| Water to make the total volume | 100 ml |

Pharmaceutical preparation 4

| Capsule: Ingredients set forth below were admixed and charged into gelatin capsules in accordance with the conventional method to thereby prepare a capsule. | |
|---|---|
| Compound 51 | 20 mg |
| Lactose | 200 mg |
| Magnesium stearate | 5 mg |

What is claimed is:

1. An s-triazolo[3,4-i]purine compound represented by the formula

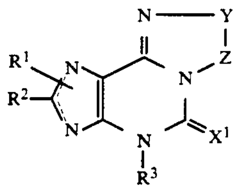

wherein Y-Z represents

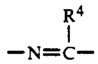 or 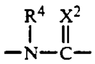

where $R^4$ represents hydrogen, alkyl, substituted or unsubstituted aromatic heterocyclic group or substituted or unsubstituted aryl; and $X^2$ represents oxygen, sulfur or NH;

each of $R^1$ and $R^2$ independently represents hydrogen, alkyl, cycloalkyl, aralkyl or substituted or unsubsituted aryl;

$R^3$ represents alkyl, cycloalkyl, aralkyl or substituted or unsubstituted aryl;

$X^1$ represents oxygen or sulfur;

and · · · · represents a single bond or a double bond or a pharmaceutically acceptable salt thereof.

2. A compound according to claim 1, wherein Y-Z represents

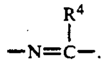

3. A compound according to claim 2, wherein $R^4$ is substituted or unsubstituted aromatic heterocyclic group; each of $R^1$ and $R^2$ independently represents hydrogen, alkyl, cycloalyky or aralkyl; $R^3$ represents alkyl or aralkyl; and $X^1$ is oxygen.

4. A compound according to claim 3, wherein $R^4$ is unsubstituted or substituted pyridyl.

5. A compound according to claim 4, which is selected from the group consisting of 6,9-dihydro-9-methyl-6-n-propyl-3-(4-pyridyl)-5H-1,2,4-triazolo[3,4-i]purin -5-one;

6,9-dihydro-9-methyl-6-n-propyl-3-(3-pyridyl)-5H-1,2,4-triazolo[3,4-i]purin-5-one;

6,9-dihydro-6-n-propyl-3-(4-pyridyl) -5H-1,2,4-triazolo[3,4-i]purin-5-one 6,9-dihydro-6-n-propyl-3-(3-pyridyl) -5H-1,2,4-triazolo[3,4-i]purin-5-one;

6-benzyl-6,9-dihydro-3-(4-pyridyl) -5H-1,2,4-triazolo[3,4-i]purin-5-one;

6-n-butyl-6,9-dihydro-3-(4-pyridyl) -5H-1,2,4-triazolo[3,4-i]purin-5-one;

9-benzyl-6,9-dihydro-6-n-propyl-3-(4-pyridyl)-5H-1,2,4-triazolo[3,4-i]purin-5-one; and 6,9-dihydro-6,9-di-n-propyl-3-(4-pyridyl) -5H-1,2,4-triazolo[3,4-i]purin-5-one.

6. A compound according to claim 1, wherein Y-Z represents

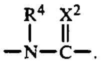

7. A compound according to claim 6, wherein $R^4$ is hydrogen or alkyl; $X^2$ is oxygen; each of $R^1$ and $R^2$ independently represents hydrogen, alkyl or cycloalkyl; $R^3$ is alkyl; and $X^1$ is oxygen.

8. A compound according to claim 7, which is 9-methyl-6-n-propyl-2,5,6,9-tetrahydro-3H -1,2,4-triazolo[3,4-i]purin-3,5-dione or 6-n-butyl-9-methyl-2,5,6,9-tetrahydro -3H-1,2,4-triazolo[3,4-i1purin-3,5-dione or 6-n-butyl9-methyl-2,5,6,9-tetrahydro -3H-1,2,4-triazolo[3,4-i]purin -3,5-dione.

9. A compound according to claim 1, wherein said salt is selected from the group consisting of pharmaceutically acceptable acid addition salt, metal salt, ammonium salt, organic amine addition salt and amino acid addition salt.

10. A pharmaceutical composition comprising a pharmaceutical carrier and as an active ingredient, an effective amount of the compound as defined by claim 1.

* * * * *

UNITED STATES PATENT AND TRADEMARK OFFICE
CERTIFICATE OF CORRECTION

PATENT NO. : 5,173,492

DATED : December 22, 1992

INVENTOR(S) : FUMIO SUZUKI ET AL.

It is certified that error appears in the above-identified patent and that said Letters Patent is hereby corrected as shown below:

TITLE PAGE

AT [75] INVENTORS

"Kazuihiro Kubo" shuold read --Kazuhiro Kubo--.

AT [57] ABSTRACT

"...." should read --,,,,--.

COLUMN 1

Line 52, "X-Z" should read --Y-Z--.

COLUMN 2

Line 1, "...." should read --,,,--.

COLUMN 5

Line 62, "wherein" should read --wherein Y-Z is--.

COLUMN 7

Line 61, "Y-Z" should read --Y-Z is--.

COLUMN 23

Line 28, "send" should read --sent--.

COLUMN 24

Line 2, "mice" should read --mice which--.

UNITED STATES PATENT AND TRADEMARK OFFICE
CERTIFICATE OF CORRECTION

PATENT NO. : 5,173,492

DATED : December 22, 1992

INVENTOR(S) : FUMIO SUZUKI ET AL.

It is certified that error appears in the above-identified patent and that said Letters Patent is hereby corrected as shown below:

COLUMN 26

Line 16, "compound" should read --compounds--.
Line 31, "-propyl -5H-" should read -- -propyl-5H- --.
Line 32, "4-i]-5-one" should read --4-i]purin-5-one-- and "1)" should read --1):--.
Line 52, "C59.88" should read --C58.88--.

COLUMN 27

Line 20, "2)" should read --2):--.

COLUMN 28

Line 27, "-methyl -6-n" should read -- -methyl-6-n--.
Line 31, "-methyl -6-n" should read -- -methyl-6-n--.
Line 67, "propyl-H" should read --propyl-5H--.

COLUMN 29

Line 3, "-methyl -6-n" should read -- -methyl-6-n--.

COLUMN 31

Line 62, "23)" should read --23):--.

COLUMN 32

Line 59, "(101)." should read --(10:1).--.

UNITED STATES PATENT AND TRADEMARK OFFICE

CERTIFICATE OF CORRECTION

PATENT NO. : 5,173,492

DATED : December 22, 1992

INVENTOR(S) : FUMIO SUZUKI ET AL.

It is certified that error appears in the above-identified patent and that said Letters Patent is hereby corrected as shown below:

COLUMN 33

Line 11, "24)" should read --24):--.
Line 43, "-5H -1,2,4-" should read -- -5H-1,2,4- --.
Line 44, "25)" should read --25):--.

COLUMN 34

Line 7, "26)" should read --26):--.
Line 48, "27)" should read --27):--.

COLUMN 35

Line 12, "28)" should read --28):--.
Line 31, "-5H -1,2,4-" should read -- -5H-1,2,4- --.
Line 32, "29)" should read --29):--.
Line 51, "-5H -1,2,4-" should read -- -5H-1,2,4- --.
Line 52, "30)" should read --30):--.

COLUMN 36

Line 24, "-pyridyl) -5H-" should read -- -pyridyl)-5H- --.
Line 25, "31)" should read --31):--.

Line 55, "32)" should read --32):--.
Line 62, "-5H -1,2,4-" should read -- -5H-1,2,4- --.

UNITED STATES PATENT AND TRADEMARK OFFICE

CERTIFICATE OF CORRECTION

PATENT NO. : 5,173,492

DATED : December 22, 1992

INVENTOR(S) : FUMIO SUZUKI ET AL.

It is certified that error appears in the above-identified patent and that said Letters Patent is hereby corrected as shown below:

COLUMN 37

Line 21, "(2-thienyl) -5H-" should read --(2-thienyl)-5H- --.
Line 22, "triazoloz-5" should read --triazolo-[3,4-i]purin-5-- and "33)" should read --33):--.
Line 27, "8benzyloxymethyl-6," should read --8-benzyloxymethyl-6,--.
Line 55, "34)" should read --34):--.

COLUMN 38

Line 7, "-phenyl -5H" should read -- -phenyl-5H--.
Line 8, "35)" should read --35):--.
Line 21, "eva.porated" should read --evaporated--.
Line 41, "36)" should read --36):--.
Line 58, "37)" should read --37):--.

COLUMN 39

Line 10, "-triazo" should read -- -triazolo- --.
Line 11, "38)" should read --38):--.
Line 36, close up right margin.
Line 37, close up left margin.
Line 42, "4triazolo[3,4-i]purin-" should read --4-triazolo[3,4-i]purin- -- and "39)" should read --39):--.
Line 64, "40)" should read --40):--.

UNITED STATES PATENT AND TRADEMARK OFFICE

CERTIFICATE OF CORRECTION

PATENT NO. : 5,173,492

DATED : December 22, 1992

INVENTOR(S) : FUMIO SUZUKI ET AL.

It is certified that error appears in the above-identified patent and that said Letters Patent is hereby corrected as shown below:

COLUMN 40

Line 16, "chloridesaturated" should read --chloride-saturated--.
Line 35, "41)" should read --41):--.
Line 58, "42)" should read --42):--.

COLUMN 41

Line 11, "4triazolo[3,.4-i]purin" should read --4-triazolo[3,4-i]purin-- and "43)" should read --43):--.
Line 30, "44)" should read --44):--.
Line 50, "45)" should read --45):--.
Line 56, "4-i]purin-3.5-dione" should read --4-i]purin-3,5-dione--.

COLUMN 42

Line 38, "$C_{10}H_{12}N_{61os.}O.5C_2H_4O_2$." should read --$C_{10}H_{12}N_6OS \cdot 0.5C_2H_4O_2$.--.
Line 45, "s, 1H)," should read --13.96(brs, 1H),--.
Line 50, "47)" should read --47):--.

COLUMN 43

Line 4, "48)" should read --48):--.
Line 36, "49)" should read --49):--.
Line 54, "50)" should read --50):--.

UNITED STATES PATENT AND TRADEMARK OFFICE

CERTIFICATE OF CORRECTION

PATENT NO. : 5,173,492

DATED : December 22, 1992

INVENTOR(S) : FUMIO SUZUKI ET AL.

It is certified that error appears in the above-identified patent and that said Letters Patent is hereby corrected as shown below:

COLUMN 44

Line 6, "triazolo3,4-i]purin" should read --triazolo[3,4-i]purin-- and "51)" should read --51):--.
Line 25, "a)" should read --a):--.
Line 31, "propyl6" should read --propyl-6--.
Line 56, "b)" should read --b):--.

COLUMN 45

Line 21, "c)" should read --c):--.
Line 22, "propyl2," should read --propyl-2,--.
Line 50, "386 (t," should read --3.86 (t,--.
Line 62, "werecol-" should read --were col- --.

COLUMN 46

Line 14, "1204(brs," should read --12.04(brs,--.
Line 21, "e)" should read --e):--.
Line 42, "f)" should read --f):--.

COLUMN 47

Line 3, "g)" should read --g):--.
Line 17, "i)" should read --i):--.
Line 54, "j)" should read --j):--.
Line 68, "l)" should read --l):--.

UNITED STATES PATENT AND TRADEMARK OFFICE
CERTIFICATE OF CORRECTION

PATENT NO. : 5,173,492
DATED : December 22, 1992
INVENTOR(S) : FUMIO SUZUKI ET AL.

It is certified that error appears in the above-identified patent and that said Letters Patent is hereby corrected as shown below:

COLUMN 48

Line 7, "compound (" should read --compound 1--.
Line 15, "(cm$^{-1}$)" should read --(cm$^{-1}$):--.
Line 23, ""(cm$^{-1}$)" should read --(cm$^{-1}$):--.
Line 26, "139 6," should read --139.6,--.
Line 33, "m)" should read --n):--.
Line 47, "n)" should read --n):--.
Line 63, "o)" should read --o):--.

COLUMN 49

Line 17, "p)" should read --p):--.
Line 32, "q)" should read --q):--.
Line 51, "r)" should read --r):--.
Line 64, "s)" should read --s):--.

COLUMN 50

Line 10, "t)" should read --t):--.
Line 23, "u)" should read --u):--.
Line 54, "Lacrose" should read --Lactose--.

COLUMN 51

Line 40, "...." should read --...--.

UNITED STATES PATENT AND TRADEMARK OFFICE

CERTIFICATE OF CORRECTION

PATENT NO. : 5,173,492

DATED : December 22, 1992

INVENTOR(S) : FUMIO SUZUKI ET AL.

It is certified that error appears in the above-identified patent and that said Letters Patent is hereby corrected as shown below:

COLUMN 52

Line 12, "(4-pyridyl) -5H" should read --(4-pyridyl)-5H--.
Line 14, "(3-pyridyl) -5H" should read --(3-pyridyl)-5H--.
Line 16, "(4-pyridyl) -5H" should read --(4-pyridyl)-5H--.
Line 18, "(4-pyridyl) -5H" should read --(4-pyridyl)-5H--.
Line 22, "(4-pyridyl) -5H" should read --(4-pyridyl)-5H--.
Line 37, "-3H -1," should read -- -3H-1,--.
Line 39, "tetrahydro -3H-1," should read --tetrahydro-3H-1,-- and "[3,4-ilpurin-3,5-" should read --[3,4-i]purin-3,5-dione--.
Lines 40-41, should be deleted.

Signed and Sealed this

Twelfth Day of October, 1993

Attest:

BRUCE LEHMAN

Attesting Officer

Commissioner of Patents and Trademarks